US009839580B2

(12) United States Patent
Lev et al.

(10) Patent No.: US 9,839,580 B2
(45) Date of Patent: Dec. 12, 2017

(54) LIQUID DRUG TRANSFER DEVICES

(71) Applicant: MEDIMOP Medical Projects Ltd., Ra'anana (IL)

(72) Inventors: Nimrod Lev, Savion (IL); Niv Ben Shalom, Netanya (IL)

(73) Assignee: Medimop Medical Projects, Ltd., Ra'anana (IL)

( * ) Notice: Subject to any disclaimer, the term of this patent is extended or adjusted under 35 U.S.C. 154(b) by 398 days.

(21) Appl. No.: 14/423,595

(22) PCT Filed: Aug. 20, 2013

(86) PCT No.: PCT/IL2013/050706
§ 371 (c)(1),
(2) Date: Feb. 24, 2015

(87) PCT Pub. No.: WO2014/033706
PCT Pub. Date: Mar. 6, 2014

(65) Prior Publication Data

US 2015/0209230 A1 Jul. 30, 2015

Related U.S. Application Data

(60) Provisional application No. 61/731,574, filed on Nov. 30, 2012.

(30) Foreign Application Priority Data

Aug. 26, 2012 (IL) .......................................... 221634

(51) Int. Cl.
*A61B 19/00* (2006.01)
*A61J 1/20* (2006.01)
(Continued)

(52) U.S. Cl.
CPC ............... *A61J 1/20* (2013.01); *A61J 1/1406* (2013.01); *A61J 1/2055* (2015.05); *A61J 1/2089* (2013.01);
(Continued)

(58) Field of Classification Search
CPC .... A61J 1/20; A61J 1/10; A61J 1/1406; A61J 1/1481; A61J 1/2089; A61J 1/2096;
(Continued)

(56) References Cited

U.S. PATENT DOCUMENTS 62,333 A 2/1867 Holl
2,247,975 A 10/1881 Wickes
(Continued)

FOREIGN PATENT DOCUMENTS

CN 1950049 A 4/2007
DE 1913926 A1 9/1970
(Continued)

OTHER PUBLICATIONS

Office Action dated Mar. 6, 2012 in U.S. Appl. No. 12/678,928.
(Continued)

*Primary Examiner* — Philip R Wiest
(74) *Attorney, Agent, or Firm* — Panitch Schwarze Belisario & Nadel LLP

(57) ABSTRACT

Liquid drug transfer devices with universal drug vial adapters for use with a drug vial of a small drug vial and a large drug vial. Some universal drug vial adapters employ the same generally opposite upright flex members for clamping a small drug vial and a large drug vial. Other universal drug vial adapters include a set of minor flex members for clamping a small drug vial and a set of major flex members encircling the set of minor flex members for clamping a large drug vial whereupon the large drug vial underlies the set of minor flex members. Liquid drug transfer devices with a universal injection port connector for attachment on an injection port of an infusion bag.

15 Claims, 26 Drawing Sheets

(51) Int. Cl.
*A61J 1/14* (2006.01)
*A61J 1/10* (2006.01)

(52) U.S. Cl.
CPC ................ *A61J 1/2096* (2013.01); *A61J 1/10* (2013.01); *A61J 1/201* (2015.05); *A61J 1/2013* (2015.05); *A61J 1/2048* (2015.05); *A61J 1/2051* (2015.05)

(58) Field of Classification Search
CPC ........ A61J 1/1487; A61J 1/201; A61J 1/2013; A61J 1/2048; A61J 1/2051; A61J 1/2055
USPC .................................................. 604/403–416
See application file for complete search history.

(56) References Cited

U.S. PATENT DOCUMENTS

| | | | |
|---|---|---|---|
| 300,060 | A | 6/1884 | Ford |
| 1,021,681 | A | 3/1912 | Jennings |
| 1,704,817 | A | 3/1929 | Ayers |
| 1,930,944 | A | 10/1933 | Schmitz, Jr. |
| 2,326,490 | A | 8/1943 | Perelson |
| 2,560,162 | A | 7/1951 | Garwood |
| 2,748,769 | A | 6/1956 | Huber |
| 2,830,587 | A | 4/1958 | Everett |
| 2,931,668 | A | 4/1960 | Baley |
| 2,968,497 | A | 1/1961 | Treleman |
| 3,059,643 | A | 10/1962 | Barton |
| D198,499 | S | 6/1964 | Harautuneian |
| 3,225,763 | A | 12/1965 | Waterman |
| 3,254,444 | A | 6/1966 | Vogel |
| 3,277,893 | A | 10/1966 | Clark |
| 3,308,822 | A | 3/1967 | De Luca |
| 3,484,849 | A | 12/1969 | Huebner et al. |
| 3,618,637 | A | 11/1971 | Santomieri |
| 3,757,981 | A | 9/1973 | Harris, Sr. et al. |
| 3,788,524 | A | 1/1974 | Davis et al. |
| 3,822,700 | A | 7/1974 | Pennington |
| 3,826,261 | A | 7/1974 | Killinger |
| 3,872,992 | A | 3/1975 | Larson |
| 3,885,607 | A | 5/1975 | Peltier |
| 3,938,520 | A | 2/1976 | Scislowicz et al. |
| 3,957,052 | A | 5/1976 | Topham |
| 3,977,555 | A | 8/1976 | Larson |
| 3,993,063 | A | 11/1976 | Larrabee |
| 4,020,839 | A | 5/1977 | Klapp |
| 4,051,852 | A | 10/1977 | Villari |
| D247,975 | S | 5/1978 | Luther |
| D248,568 | S | 7/1978 | Ismach |
| 4,109,670 | A | 8/1978 | Slagel |
| 4,121,585 | A | 10/1978 | Becker, Jr. |
| 4,161,178 | A | 7/1979 | Genese |
| 4,187,848 | A | 2/1980 | Taylor |
| D254,444 | S | 3/1980 | Levine |
| 4,203,067 | A | 5/1980 | Fitzky et al. |
| 4,203,443 | A | 5/1980 | Genese |
| 4,210,173 | A | 7/1980 | Choksi et al. |
| D257,286 | S | 10/1980 | Folkman |
| 4,253,501 | A | 3/1981 | Ogle |
| 4,296,786 | A | 10/1981 | Brignola |
| 4,303,067 | A | 12/1981 | Connolly et al. |
| 4,312,349 | A | 1/1982 | Cohen |
| 4,314,586 | A | 2/1982 | Folkman |
| 4,328,802 | A | 5/1982 | Curley et al. |
| 4,335,717 | A | 6/1982 | Bujan et al. |
| D267,199 | S | 12/1982 | Koenig |
| 4,376,634 | A | 3/1983 | Prior et al. |
| D268,871 | S | 5/1983 | Benham et al. |
| 4,392,850 | A | 7/1983 | Elias et al. |
| D270,282 | S | 8/1983 | Gross |
| 4,410,321 | A | 10/1983 | Pearson et al. |
| 4,411,662 | A | 10/1983 | Pearson |
| D271,421 | S | 11/1983 | Fetterman |
| 4,434,823 | A | 3/1984 | Hudspith |
| 4,465,471 | A | 8/1984 | Harris et al. |
| 4,475,915 | A | 10/1984 | Sloane |
| 4,493,348 | A | 1/1985 | Lemmons |
| 4,505,709 | A | 3/1985 | Froning et al. |
| 4,507,113 | A | 3/1985 | Dunlap |
| D280,018 | S | 8/1985 | Scott |
| 4,532,969 | A | 8/1985 | Kwaan |
| 4,564,054 | A | 1/1986 | Gustaysson |
| 4,573,993 | A | 3/1986 | Hoag et al. |
| 4,576,211 | A | 3/1986 | Valentini et al. |
| 4,581,014 | A | 4/1986 | Millerd et al. |
| 4,585,446 | A | 4/1986 | Kempf |
| 4,588,396 | A | 5/1986 | Stroebel et al. |
| 4,588,403 | A | 5/1986 | Weiss et al. |
| D284,603 | S | 7/1986 | Loignon |
| 4,604,093 | A | 8/1986 | Brown et al. |
| 4,607,671 | A | 8/1986 | Aalto et al. |
| 4,614,437 | A | 9/1986 | Buehler |
| 4,638,975 | A | 1/1987 | Iuchi et al. |
| 4,639,019 | A | 1/1987 | Mittleman |
| 4,667,927 | A | 5/1987 | Oscarsson |
| 4,675,020 | A | 6/1987 | McPhee |
| 4,676,530 | A | 6/1987 | Nordgren et al. |
| 4,683,975 | A | 8/1987 | Booth et al. |
| 4,697,622 | A | 10/1987 | Swift et al. |
| 4,721,133 | A | 1/1988 | Sundblom |
| 4,729,401 | A | 3/1988 | Raines |
| 4,735,608 | A | 4/1988 | Sardam |
| 4,743,229 | A | 5/1988 | Chu |
| 4,743,243 | A | 5/1988 | Vaillancourt |
| 4,752,292 | A | 6/1988 | Lopez et al. |
| 4,758,235 | A | 7/1988 | Tu |
| 4,759,756 | A | 7/1988 | Forman et al. |
| 4,778,447 | A | 10/1988 | Velde et al. |
| 4,787,898 | A | 11/1988 | Raines |
| 4,797,898 | A | 1/1989 | Martinez |
| D300,060 | S | 2/1989 | Molgaard-Nielsen |
| 4,804,366 | A | 2/1989 | Zdeb et al. |
| 4,826,492 | A | 5/1989 | Magasi |
| 4,832,690 | A | 5/1989 | Kuu |
| 4,834,152 | A | 5/1989 | Howson et al. |
| D303,013 | S | 8/1989 | Konopka |
| 4,857,062 | A | 8/1989 | Russell |
| 4,865,592 | A | 9/1989 | Rycroft |
| 4,871,463 | A | 10/1989 | Taylor et al. |
| 4,898,209 | A | 2/1990 | Zbed |
| 4,909,290 | A | 3/1990 | Coccia |
| 4,927,423 | A | 5/1990 | Malmborg |
| 4,931,040 | A | 6/1990 | Haber et al. |
| 4,932,944 | A | 6/1990 | Jagger et al. |
| 4,967,797 | A | 11/1990 | Manska |
| D314,050 | S | 1/1991 | Sone |
| D314,622 | S | 2/1991 | Andersson et al. |
| 4,997,430 | A | 3/1991 | Van der Heiden et al. |
| 5,006,114 | A | 4/1991 | Rogers et al. |
| 5,035,686 | A | 7/1991 | Crittenden et al. |
| 5,041,105 | A | 8/1991 | D'Alo et al. |
| 5,045,066 | A | 9/1991 | Scheuble et al. |
| 5,049,129 | A | 9/1991 | Zdeb et al. |
| 5,053,015 | A | 10/1991 | Gross |
| 5,061,248 | A | 10/1991 | Sacco |
| 5,088,996 | A | 2/1992 | Kopfer et al. |
| 5,096,575 | A | 3/1992 | Cosack |
| 5,104,387 | A | 4/1992 | Pokorney et al. |
| 5,113,904 | A | 5/1992 | Aslanian |
| 5,122,124 | A | 6/1992 | Novacek et al. |
| 5,125,908 | A | 6/1992 | Cohen |
| 5,125,915 | A | 6/1992 | Berry et al. |
| D328,788 | S | 8/1992 | Sagae et al. |
| 5,171,230 | A | 12/1992 | Eland et al. |
| 5,201,705 | A | 4/1993 | Berglund et al. |
| 5,201,717 | A | 4/1993 | Wyatt et al. |
| 5,203,771 | A | 4/1993 | Melker et al. |
| 5,203,775 | A | 4/1993 | Frank et al. |
| 5,211,638 | A | 5/1993 | Dudar et al. |
| 5,232,029 | A | 8/1993 | Knox et al. |
| 5,232,109 | A | 8/1993 | Tirrell et al. |
| 5,242,432 | A | 9/1993 | DeFrank |
| 5,247,972 | A | 9/1993 | Tetreault |
| D341,420 | S | 11/1993 | Conn |

(56) References Cited

U.S. PATENT DOCUMENTS

| | | | |
|---|---|---|---|
| 5,269,768 | A | 12/1993 | Cheung |
| 5,270,219 | A | 12/1993 | DeCastro et al. |
| 5,279,576 | A | 1/1994 | Loo et al. |
| 5,288,290 | A | 2/1994 | Brody |
| 5,300,034 | A | 4/1994 | Behnke et al. |
| 5,301,685 | A | 4/1994 | Guirguis |
| 5,304,163 | A | 4/1994 | Bonnici et al. |
| 5,304,165 | A | 4/1994 | Haber et al. |
| 5,308,483 | A | 5/1994 | Sklar et al. |
| 5,312,377 | A | 5/1994 | Dalton |
| 5,328,474 | A | 7/1994 | Raines |
| D349,648 | S | 8/1994 | Tirrell et al. |
| 5,334,163 | A | 8/1994 | Sinnett |
| 5,334,179 | A | 8/1994 | Poli et al. |
| 5,342,346 | A | 8/1994 | Honda et al. |
| 5,344,417 | A | 9/1994 | Wadsworth, Jr. |
| 5,348,548 | A | 9/1994 | Meyer et al. |
| 5,350,372 | A | 9/1994 | Ikeda et al. |
| 5,364,386 | A | 11/1994 | Fukuoka et al. |
| 5,364,387 | A | 11/1994 | Sweeney |
| 5,374,264 | A | 12/1994 | Wadsworth, Jr. |
| 5,385,547 | A | 1/1995 | Wong et al. |
| 5,397,303 | A | 3/1995 | Sancoff et al. |
| D357,733 | S | 4/1995 | Matkovich |
| 5,429,614 | A | 7/1995 | Fowles et al. |
| 5,433,330 | A | 7/1995 | Yatsko et al. |
| 5,445,630 | A | 8/1995 | Richmond |
| 5,445,631 | A | 8/1995 | Uchida |
| D362,718 | S | 9/1995 | Deily et al. |
| 5,451,374 | A | 9/1995 | Molina |
| 5,454,805 | A | 10/1995 | Brony |
| 5,464,111 | A | 11/1995 | Vacek et al. |
| 5,464,123 | A | 11/1995 | Scarrow |
| 5,466,219 | A | 11/1995 | Lynn et al. |
| 5,466,220 | A | 11/1995 | Brenneman |
| 5,470,327 | A | 11/1995 | Helgren et al. |
| 5,471,994 | A | 12/1995 | Guirguis |
| 5,472,022 | A | 12/1995 | Michel et al. |
| 5,478,337 | A | 12/1995 | Okamoto et al. |
| 5,492,147 | A | 2/1996 | Challender et al. |
| D369,406 | S | 4/1996 | Niedospial et al. |
| 5,505,714 | A | 4/1996 | Dassa et al. |
| 5,509,433 | A | 4/1996 | Paradis |
| 5,515,871 | A | 5/1996 | Bittner et al. |
| 5,520,659 | A | 5/1996 | Hedges |
| 5,526,853 | A | 6/1996 | McPhee et al. |
| 5,527,306 | A | 6/1996 | Haining |
| 5,531,695 | A | 7/1996 | Swisher |
| 5,547,471 | A | 8/1996 | Thompson et al. |
| 5,549,577 | A | 8/1996 | Siegel et al. |
| 5,554,128 | A | 9/1996 | Hedges |
| 5,562,696 | A | 10/1996 | Nobles et al. |
| 5,566,729 | A | 10/1996 | Grabenkort et al. |
| 5,569,191 | A | 10/1996 | Meyer |
| 5,573,281 | A | 11/1996 | Keller |
| 5,578,015 | A | 11/1996 | Robb |
| 5,583,052 | A | 12/1996 | Portnoff et al. |
| 5,584,819 | A | 12/1996 | Kopfer |
| 5,591,143 | A | 1/1997 | Trombley, III et al. |
| 5,603,706 | A | 2/1997 | Wyatt et al. |
| 5,607,439 | A | 3/1997 | Yoon |
| 5,611,576 | A | 3/1997 | Guala |
| 5,616,203 | A | 4/1997 | Stevens |
| 5,636,660 | A | 6/1997 | Pfleiderer et al. |
| 5,637,101 | A | 6/1997 | Shillington |
| 5,641,010 | A | 6/1997 | Maier |
| 5,645,538 | A | 7/1997 | Richmond |
| 5,647,845 | A | 7/1997 | Haber et al. |
| 5,651,776 | A | 7/1997 | Appling et al. |
| 5,653,686 | A | 8/1997 | Coulter et al. |
| 5,674,195 | A | 10/1997 | Truthan |
| 5,676,346 | A | 10/1997 | Leinsing |
| 5,685,845 | A | 11/1997 | Grimard |
| D388,172 | S | 12/1997 | Cipes |
| 5,699,821 | A | 12/1997 | Paradis |
| 5,702,019 | A | 12/1997 | Grimard |
| 5,718,346 | A | 2/1998 | Weiler |
| D393,722 | S | 4/1998 | Fangrow, Jr. et al. |
| 5,738,144 | A | 4/1998 | Rogers |
| 5,743,312 | A | 4/1998 | Pfeifer et al. |
| 5,746,733 | A | 5/1998 | Capaccio et al. |
| 5,752,942 | A | 5/1998 | Doyle et al. |
| 5,755,696 | A | 5/1998 | Caizza |
| 5,766,211 | A | 6/1998 | Wood et al. |
| 5,772,630 | A | 6/1998 | Ljungquist |
| 5,772,652 | A | 6/1998 | Zielinski |
| RE35,841 | E | 7/1998 | Frank et al. |
| 5,776,116 | A | 7/1998 | Lopez et al. |
| 5,782,872 | A | 7/1998 | Muller |
| 5,806,831 | A | 9/1998 | Paradis |
| 5,810,792 | A | 9/1998 | Fangrow, Jr. et al. |
| D399,559 | S | 10/1998 | Molina |
| 5,817,082 | A | 10/1998 | Niedospial, Jr. et al. |
| 5,820,621 | A | 10/1998 | Yale et al. |
| 5,827,262 | A | 10/1998 | Neftel et al. |
| 5,832,971 | A | 11/1998 | Yale et al. |
| 5,833,213 | A | 11/1998 | Ryan |
| 5,834,744 | A | 11/1998 | Risman |
| 5,839,715 | A | 11/1998 | Leinsing |
| 5,853,406 | A | 12/1998 | Masuda et al. |
| D405,522 | S | 2/1999 | Hoenig et al. |
| 5,871,110 | A | 2/1999 | Grimard et al. |
| 5,873,872 | A | 2/1999 | Thibault et al. |
| 5,879,337 | A | 3/1999 | Kuracina et al. |
| 5,879,345 | A | 3/1999 | Aneas |
| 5,887,633 | A | 3/1999 | Yale et al. |
| 5,890,610 | A | 4/1999 | Jansen et al. |
| 5,891,129 | A | 4/1999 | Daubert et al. |
| 5,893,397 | A | 4/1999 | Peterson et al. |
| 5,897,526 | A | 4/1999 | Vaillancourt |
| 5,899,468 | A | 5/1999 | Apps et al. |
| 5,902,280 | A | 5/1999 | Powles et al. |
| 5,902,298 | A | 5/1999 | Niedospial, Jr. et al. |
| D410,740 | S | 6/1999 | Molina |
| 5,911,710 | A | 6/1999 | Barry et al. |
| 5,919,182 | A | 7/1999 | Avallone |
| 5,921,419 | A | 7/1999 | Niedospial, Jr. et al. |
| 5,924,584 | A | 7/1999 | Hellstrom et al. |
| 5,925,029 | A | 7/1999 | Jansen et al. |
| 5,935,112 | A | 8/1999 | Stevens et al. |
| 5,941,848 | A | 8/1999 | Nishimoto et al. |
| 5,944,700 | A | 8/1999 | Nguyen et al. |
| 5,954,104 | A | 9/1999 | Daubert et al. |
| 5,968,022 | A | 10/1999 | Saito |
| 5,971,181 | A | 10/1999 | Niedospial, Jr. et al. |
| 5,971,965 | A | 10/1999 | Mayer |
| 5,989,237 | A | 11/1999 | Fowles et al. |
| 6,003,566 | A | 12/1999 | Thibault et al. |
| 6,004,278 | A | 12/1999 | Botich et al. |
| 6,019,750 | A | 2/2000 | Fowles et al. |
| 6,022,339 | A | 2/2000 | Fowles et al. |
| 6,036,171 | A | 3/2000 | Weinheimer et al. |
| 6,039,093 | A | 3/2000 | Mrotzek et al. |
| 6,039,302 | A | 3/2000 | Cote, Sr. et al. |
| D422,357 | S | 4/2000 | Niedospial, Jr. et al. |
| 6,063,068 | A | 5/2000 | Fowles et al. |
| D427,308 | S | 6/2000 | Zinger |
| D427,309 | S | 6/2000 | Molina |
| 6,070,623 | A | 6/2000 | Aneas |
| 6,071,270 | A | 6/2000 | Fowles et al. |
| 6,080,132 | A | 6/2000 | Cole et al. |
| D428,141 | S | 7/2000 | Brotspies et al. |
| 6,086,762 | A | 7/2000 | Guala |
| 6,089,541 | A | 7/2000 | Weinheimer et al. |
| 6,090,091 | A | 7/2000 | Fowles et al. |
| 6,090,093 | A | 7/2000 | Thibault et al. |
| 6,092,692 | A | 7/2000 | Riskin |
| D430,291 | S | 8/2000 | Jansen et al. |
| 6,099,511 | A | 8/2000 | Devos et al. |
| 6,113,068 | A | 9/2000 | Ryan |
| 6,113,583 | A | 9/2000 | Fowles et al. |
| 6,117,114 | A | 9/2000 | Paradis |
| D431,864 | S | 10/2000 | Jansen |
| 6,139,534 | A | 10/2000 | Niedospial, Jr. et al. |

(56) References Cited

U.S. PATENT DOCUMENTS 6,142,446 A 11/2000 Leinsing
6,146,362 A 11/2000 Turnbull et al.
6,149,623 A 11/2000 Reynolds
6,156,025 A 12/2000 Niedospial, Jr. et al.
6,159,192 A 12/2000 Fowles et al.
6,168,037 B1 1/2001 Grimard
6,171,287 B1 1/2001 Lynn et al.
6,171,293 B1 1/2001 Rowley et al.
6,173,852 B1 1/2001 Browne
6,173,868 B1 1/2001 DeJonge
6,174,304 B1 1/2001 Weston
6,179,822 B1 1/2001 Niedospial, Jr.
6,179,823 B1 1/2001 Niedospial, Jr.
6,206,861 B1 3/2001 Mayer
6,221,041 B1 4/2001 Russo
6,221,054 B1 4/2001 Martin et al.
6,221,065 B1 4/2001 Davis
6,238,372 B1 5/2001 Zinger et al.
6,245,044 B1 6/2001 Daw et al.
D445,501 S 7/2001 Niedospial, Jr.
D445,895 S 7/2001 Svendsen
6,253,804 B1 7/2001 Safabash
6,258,078 B1 7/2001 Thilly
6,280,430 B1 8/2001 Neftel et al.
6,290,688 B1 9/2001 Lopez et al.
6,296,621 B1 10/2001 Masuda et al.
6,299,131 B1 10/2001 Ryan
6,343,629 B1 2/2002 Wessman et al.
6,348,044 B1 2/2002 Coletti et al.
6,358,236 B1 3/2002 DeFoggi et al.
6,364,866 B1 4/2002 Furr et al.
6,378,576 B2 4/2002 Thibault et al.
6,378,714 B1 4/2002 Jansen et al.
6,379,340 B1 4/2002 Zinger et al.
D457,954 S 5/2002 Wallace et al.
6,382,442 B1 5/2002 Thibault et al.
6,386,397 B2 5/2002 Brotspies et al.
6,408,897 B1 6/2002 Laurent et al.
6,409,708 B1 6/2002 Wessman
6,440,107 B1 8/2002 Trombley, III et al.
6,453,949 B1 9/2002 Chau
6,453,956 B2 9/2002 Safabash
6,474,375 B2 11/2002 Spero et al.
6,478,788 B1 11/2002 Aneas
D468,015 S 12/2002 Horppu
6,499,617 B1 12/2002 Niedospial, Jr. et al.
6,503,240 B1 1/2003 Niedospial, Jr. et al.
6,503,244 B2 1/2003 Hayman
6,520,932 B2 2/2003 Taylor
6,524,278 B1 2/2003 Campbell et al.
6,524,295 B2 2/2003 Daubert et al.
D472,316 S 3/2003 Douglas et al.
6,530,903 B2 3/2003 Wang et al.
6,537,263 B1 3/2003 Aneas
D472,630 S 4/2003 Douglas et al.
6,544,246 B1 4/2003 Niedospial, Jr.
6,551,299 B2 4/2003 Miyoshi et al.
6,558,365 B2 5/2003 Zinger et al.
6,571,837 B2 6/2003 Jansen et al.
6,572,591 B2 6/2003 Mayer
6,575,955 B2 6/2003 Azzolini
6,581,593 B1 6/2003 Rubin et al.
6,582,415 B1 6/2003 Fowles et al.
D476,731 S 7/2003 Cise et al.
6,591,876 B2 7/2003 Safabash
6,599,273 B1 7/2003 Lopez
6,601,721 B2 8/2003 Jansen et al.
6,626,309 B1 9/2003 Jansen et al.
6,638,244 B1 10/2003 Reynolds
D482,121 S 11/2003 Harding et al.
D482,447 S 11/2003 Harding et al.
6,651,956 B2 11/2003 Miller
6,652,509 B1 11/2003 Helgren et al.
D483,487 S 12/2003 Harding et al.
D483,869 S 12/2003 Tran et al.
6,656,433 B2 12/2003 Sasso
6,666,852 B2 12/2003 Niedospial, Jr.
6,681,810 B2 1/2004 Weston
6,681,946 B1 1/2004 Jansen et al.
6,682,509 B2 1/2004 Lopez
6,692,478 B1 2/2004 Paradis
6,692,829 B2 2/2004 Stubler et al.
6,695,829 B2 2/2004 Hellstrom et al.
6,699,229 B2 3/2004 Zinger et al.
6,706,022 B1 3/2004 Leinsing et al.
6,706,031 B2 3/2004 Manera
6,715,520 B2 4/2004 Andreasson et al.
6,729,370 B2 5/2004 Norton et al.
6,736,798 B2 5/2004 Ohkubo et al.
6,745,998 B2 6/2004 Doyle
6,746,438 B1 6/2004 Arnissolle
6,752,180 B2 6/2004 Delay
D495,416 S 8/2004 Dimeo et al.
D496,457 S 9/2004 Prais et al.
6,802,490 B2 10/2004 Leinsing et al.
6,832,994 B2 12/2004 Niedospial, Jr. et al.
6,852,103 B2 2/2005 Fowles et al.
6,875,203 B1 4/2005 Fowles et al.
6,875,205 B2 4/2005 Leinsing
6,878,131 B2 4/2005 Novacek et al.
6,884,253 B1 4/2005 McFarlane
6,890,328 B2 5/2005 Fowles et al.
D506,256 S 6/2005 Miyoshi et al.
6,901,975 B2 6/2005 Aramata et al.
6,945,417 B2 9/2005 Jansen et al.
6,948,522 B2 9/2005 Newbrough et al.
6,949,086 B2 9/2005 Ferguson et al.
6,951,613 B2 10/2005 Reif et al.
6,957,745 B2 10/2005 Thibault et al.
6,960,164 B2 11/2005 O'Heeron
6,979,318 B1 12/2005 McDonald et al.
RE38,996 E 2/2006 Crawford et al.
6,994,315 B2 2/2006 Ryan et al.
6,997,916 B2 2/2006 Simas, Jr. et al.
6,997,917 B2 2/2006 Niedospial, Jr. et al.
7,024,968 B2 4/2006 Raudabough et al.
7,070,589 B2 7/2006 Lolachi et al.
7,074,216 B2 7/2006 Fowles et al.
7,083,600 B2 8/2006 Meloul
7,086,431 B2 8/2006 D'Antonio et al.
7,100,890 B2 9/2006 Cote, Sr. et al.
7,140,401 B2 11/2006 Wilcox et al.
7,150,735 B2 12/2006 Hickle
7,192,423 B2 3/2007 Wong
7,195,623 B2 3/2007 Burroughs et al.
7,241,285 B1 7/2007 Dikeman
7,294,122 B2 11/2007 Kubo et al.
7,306,199 B2 12/2007 Leinsing et al.
D561,348 S 2/2008 Zinger et al.
7,326,188 B1 2/2008 Russell et al.
7,326,194 B2 2/2008 Zinger et al.
7,350,764 B2 4/2008 Raybuck
7,354,422 B2 4/2008 Riesenberger et al.
7,354,427 B2 4/2008 Fangrow
7,425,209 B2 9/2008 Fowles et al.
7,435,246 B2 10/2008 Zihlmann
D580,558 S 11/2008 Shigesada et al.
7,452,348 B2 11/2008 Hasegawa
7,470,257 B2 12/2008 Norton et al.
7,470,265 B2 12/2008 Brugger et al.
7,472,932 B2 1/2009 Weber et al.
7,488,297 B2 2/2009 Flaherty
7,491,197 B2 2/2009 Jansen et al.
7,497,848 B2 3/2009 Leinsing et al.
7,523,967 B2 4/2009 Steppe
7,530,546 B2 5/2009 Ryan et al.
D595,420 S 6/2009 Suzuki et al.
D595,421 S 6/2009 Suzuki et al.
7,540,863 B2 6/2009 Haindl
7,540,865 B2 6/2009 Griffin et al.
7,544,191 B2 6/2009 Peluso et al.
D595,862 S 7/2009 Suzuki et al.
D595,863 S 7/2009 Suzuki et al.
7,611,487 B2 11/2009 Woehr et al.

(56) References Cited

U.S. PATENT DOCUMENTS 7,611,502 B2 11/2009 Daly
7,615,041 B2 11/2009 Sullivan et al.
7,628,779 B2 12/2009 Aneas
7,632,261 B2 12/2009 Zinger et al.
D608,900 S 1/2010 Giraud et al.
7,654,995 B2 2/2010 Warren et al.
7,670,326 B2 3/2010 Shemesh
7,695,445 B2 4/2010 Yuki
D616,090 S 5/2010 Kawamura
7,713,247 B2 5/2010 Lopez
7,717,886 B2 5/2010 Lopez
7,722,090 B2 5/2010 Burton et al.
D616,984 S 6/2010 Gilboa
7,731,678 B2 6/2010 Tennican et al.
7,743,799 B2 6/2010 Mosler et al.
7,744,581 B2 6/2010 Wallen et al.
7,757,901 B2 7/2010 Welp
7,758,082 B2 7/2010 Weigel et al.
7,758,560 B2 7/2010 Connell et al.
7,762,524 B2 7/2010 Cawthon et al.
7,766,304 B2 8/2010 Phillips
7,771,383 B2 8/2010 Truitt et al.
D624,641 S 9/2010 Boclet
7,799,009 B2 9/2010 Niedospial, Jr. et al.
7,803,140 B2 9/2010 Fangrow, Jr.
D627,216 S 11/2010 Fulginiti
D630,732 S 1/2011 Lev et al.
7,862,537 B2 1/2011 Zinger et al.
7,867,215 B2 1/2011 Akerlund et al.
7,879,018 B2 2/2011 Zinger et al.
7,895,216 B2 2/2011 Longshaw et al.
D634,007 S 3/2011 Zinger et al.
7,900,659 B2 3/2011 Whitley et al.
D637,713 S 5/2011 Nord et al.
D641,080 S 7/2011 Zinger et al.
7,985,216 B2 7/2011 Daily et al.
D644,104 S 8/2011 Maeda et al.
7,993,328 B2 8/2011 Whitley
8,007,461 B2 8/2011 Huo et al.
8,012,132 B2 9/2011 Lum et al.
8,016,809 B2 9/2011 Zinger et al.
8,021,325 B2 9/2011 Zinger et al.
8,025,653 B2 9/2011 Capitaine et al.
8,029,472 B2 10/2011 Leinsing et al.
8,038,123 B2 10/2011 Ruschke et al.
8,066,688 B2 11/2011 Zinger et al.
8,070,739 B2 12/2011 Zinger et al.
8,075,550 B2 12/2011 Nord et al.
8,096,525 B2 1/2012 Ryan
8,105,314 B2 1/2012 Fangrow, Jr.
D654,166 S 2/2012 Lair
D655,017 S 2/2012 Mosler et al.
8,122,923 B2 2/2012 Kraus et al.
8,123,736 B2 2/2012 Kraushaar et al.
D657,461 S 4/2012 Schembre et al.
8,157,784 B2 4/2012 Rogers
8,167,863 B2 5/2012 Yaw
8,172,824 B2 5/2012 Pfeifer et al.
8,177,768 B2 5/2012 Leinsing
8,182,452 B2 5/2012 Mansour et al.
8,187,248 B2 5/2012 Zihlmann
8,196,614 B2 6/2012 Kriheli
8,197,459 B2 6/2012 Jansen et al.
8,211,069 B2 7/2012 Fangrow, Jr.
8,225,959 B2 7/2012 Lambrecht
8,241,268 B2 8/2012 Whitley
8,262,628 B2 9/2012 Fangrow, Jr.
8,262,641 B2 9/2012 Vednne et al.
8,267,127 B2 9/2012 Kriheli
D669,980 S 10/2012 Lev et al.
8,287,513 B2 10/2012 Ellstrom et al.
D673,673 S 1/2013 Wang
D674,084 S 1/2013 Linnenschmidt
D674,088 S 1/2013 Lev et al.
D681,230 S 4/2013 Mosler et al.
8,454,573 B2 6/2013 Wyatt et al.
8,469,939 B2 6/2013 Fangrow, Jr.
8,475,404 B2 7/2013 Foshee et al.
8,480,645 B1 7/2013 Choudhury et al.
8,480,646 B2 7/2013 Nord et al.
8,506,548 B2 8/2013 Okiyama
8,511,352 B2 8/2013 Kraus et al.
8,512,309 B2 8/2013 Shemesh et al.
D690,009 S 9/2013 Schembre et al.
D690,418 S 9/2013 Rosenquist
8,523,837 B2 9/2013 Wiggins et al.
8,545,476 B2 10/2013 Ariagno et al.
8,551,067 B2 10/2013 Zinger et al.
8,556,879 B2 10/2013 Okiyama
8,562,582 B2 10/2013 Tuckwell et al.
8,608,723 B2 12/2013 Lev et al.
8,628,508 B2 1/2014 Weitzel et al.
8,684,992 B2 4/2014 Sullivan et al.
8,684,994 B2 4/2014 Lev et al.
8,752,598 B2 6/2014 Denenburg et al.
D714,935 S 10/2014 Nishioka et al.
D717,406 S 11/2014 Stanley et al.
D717,948 S 11/2014 Strong et al.
D719,650 S 12/2014 Arinobe et al.
D720,067 S 12/2014 Rosenquist
D720,451 S 12/2014 Denenburg et al.
D720,452 S 12/2014 Jordan
8,900,212 B2 12/2014 Kubo
D720,850 S 1/2015 Hsia et al.
D732,660 S 6/2015 Ohashi
D732,664 S 6/2015 Woehr et al.
D733,291 S 6/2015 Wang
D733,292 S 6/2015 Rogers
D733,293 S 6/2015 Rogers
D738,494 S 9/2015 Kashmirian
D741,457 S 10/2015 Guest
D750,235 S 2/2016 Maurice
2001/0000347 A1 4/2001 Hellstrom et al.
2001/0025671 A1 10/2001 Safabash
2001/0029360 A1 10/2001 Miyoshi et al.
2001/0051793 A1 12/2001 Weston
2002/0017328 A1 2/2002 Loo
2002/0066715 A1 6/2002 Niedospial
2002/0087118 A1 7/2002 Reynolds et al.
2002/0087141 A1 7/2002 Zinger et al.
2002/0087144 A1 7/2002 Zinger et al.
2002/0121496 A1 9/2002 Thiebault et al.
2002/0123736 A1 9/2002 Fowles et al.
2002/0127150 A1 9/2002 Sasso
2002/0128628 A1 9/2002 Fathallah
2002/0138045 A1 9/2002 Moen
2002/0173752 A1 11/2002 Polzin
2002/0193777 A1 12/2002 Aneas
2003/0028156 A1 2/2003 Juliar
2003/0036725 A1 2/2003 Lavi et al.
2003/0068354 A1 4/2003 Reif et al.
2003/0069550 A1 4/2003 Sharp
2003/0073971 A1 4/2003 Saker
2003/0100866 A1 5/2003 Reynolds
2003/0109846 A1 6/2003 Zinger et al.
2003/0120209 A1 6/2003 Jensen et al.
2003/0153895 A1 8/2003 Leinsing
2003/0187420 A1 10/2003 Akerlund et al.
2003/0191445 A1 10/2003 Wallen et al.
2003/0195479 A1 10/2003 Kuracina et al.
2003/0199846 A1 10/2003 Fowles et al.
2003/0199847 A1 10/2003 Akerlund et al.
2003/0205843 A1 11/2003 Adams
2003/0236543 A1 12/2003 Brenneman et al.
2004/0024354 A1 2/2004 Reynolds
2004/0039365 A1 2/2004 Aramata et al.
2004/0044327 A1 3/2004 Hasegawa
2004/0073189 A1 4/2004 Wyatt et al.
2004/0143218 A1 7/2004 Das
2004/0143226 A1 7/2004 Marsden
2004/0153047 A1 8/2004 Blank et al.
2004/0162540 A1 8/2004 Walenciak et al.
2004/0167472 A1 8/2004 Howell et al.
2004/0181192 A1 9/2004 Cuppy

(56) References Cited

U.S. PATENT DOCUMENTS

2004/0204699 A1 10/2004 Hanly et al.
2004/0217315 A1 11/2004 Doyle
2004/0225274 A1 11/2004 Jansen et al.
2004/0236305 A1 11/2004 Jansen et al.
2004/0249341 A1 12/2004 Newbrough et al.
2004/0255952 A1 12/2004 Carlsen et al.
2005/0015070 A1 1/2005 Delnevo et al.
2005/0016626 A1 1/2005 Wilcox et al.
2005/0055008 A1 3/2005 Paradis et al.
2005/0082828 A1 4/2005 Wicks et al.
2005/0124964 A1 6/2005 Niedospial et al.
2005/0137523 A1 6/2005 Wyatt et al.
2005/0137566 A1 6/2005 Fowles et al.
2005/0148994 A1 7/2005 Leinsing
2005/0159724 A1 7/2005 Enerson
2005/0182383 A1 8/2005 Wallen
2005/0209554 A1 9/2005 Landau
2005/0261637 A1 11/2005 Miller
2005/0277896 A1 12/2005 Messerli et al.
2006/0030832 A1 2/2006 Niedospial et al.
2006/0079834 A1 4/2006 Tennican et al.
2006/0089594 A1 4/2006 Landau
2006/0089603 A1 4/2006 Truitt et al.
2006/0095015 A1 5/2006 Hobbs et al.
2006/0106360 A1 5/2006 Wong
2006/0135948 A1 6/2006 Varma
2006/0155257 A1 7/2006 Reynolds
2006/0161192 A1 7/2006 Young
2006/0178646 A1 8/2006 Harris et al.
2006/0212004 A1 9/2006 Atil
2006/0253084 A1 11/2006 Nordgren
2006/0259004 A1 11/2006 Connell et al.
2007/0024995 A1 2/2007 Hayashi
2007/0060904 A1 3/2007 Vedrine et al.
2007/0078428 A1 4/2007 Reynolds et al.
2007/0079894 A1 4/2007 Kraus et al.
2007/0083164 A1 4/2007 Barrelle et al.
2007/0088252 A1 4/2007 Pestotnik et al.
2007/0088293 A1 4/2007 Fangrow
2007/0088313 A1 4/2007 Zinger et al.
2007/0106244 A1 5/2007 Mosler et al.
2007/0112324 A1 5/2007 Hamedi-Sangsari
2007/0156112 A1 7/2007 Walsh
2007/0167904 A1 7/2007 Zinger et al.
2007/0191760 A1 8/2007 Iguchi et al.
2007/0191764 A1 8/2007 Zihlmann
2007/0191767 A1 8/2007 Hennessy et al.
2007/0203451 A1 8/2007 Murakami et al.
2007/0219483 A1 9/2007 Kitani et al.
2007/0244447 A1 10/2007 Capitaine et al.
2007/0244461 A1 10/2007 Fangrow
2007/0244462 A1 10/2007 Fangrow
2007/0244463 A1 10/2007 Warren et al.
2007/0249995 A1 10/2007 Van Manen
2007/0255202 A1 11/2007 Kitani et al.
2007/0265574 A1 11/2007 Tennican et al.
2007/0265581 A1 11/2007 Funamura et al.
2007/0270778 A9 11/2007 Zinger et al.
2007/0287953 A1 12/2007 Ziv et al.
2007/0299404 A1 12/2007 Katoh et al.
2008/0009789 A1 1/2008 Zinger et al.
2008/0009822 A1 1/2008 Enerson
2008/0015496 A1 1/2008 Hamedi-Sangsari
2008/0135051 A1 6/2008 Lee
2008/0172024 A1 7/2008 Yaw
2008/0188799 A1 8/2008 Mueller-Beckhaus et al.
2008/0249479 A1 10/2008 Zinger et al.
2008/0249498 A1 10/2008 Fangrow
2008/0262465 A1 10/2008 Zinger et al.
2008/0287905 A1 11/2008 Hiejima et al.
2008/0294100 A1 11/2008 de Costa et al.
2008/0306439 A1 12/2008 Nelson et al.
2008/0312634 A1 12/2008 Helmerson et al.
2009/0012492 A1 1/2009 Zihlmann
2009/0082750 A1 3/2009 Denenburg et al.
2009/0143758 A1 6/2009 Okiyama
2009/0177177 A1 7/2009 Zinger et al.
2009/0177178 A1 7/2009 Pedersen
2009/0187140 A1 7/2009 Racz
2009/0216212 A1 8/2009 Fangrow, Jr.
2009/0267011 A1 10/2009 Hatton et al.
2009/0299325 A1 12/2009 Vedrine et al.
2009/0318946 A1 12/2009 Tamesada
2009/0326506 A1 12/2009 Hasegawa et al.
2010/0010443 A1 1/2010 Morgan et al.
2010/0016811 A1 1/2010 Smith
2010/0022985 A1 1/2010 Sullivan et al.
2010/0030181 A1 2/2010 Helle et al.
2010/0036319 A1 2/2010 Drake et al.
2010/0076397 A1 3/2010 Reed et al.
2010/0087786 A1 4/2010 Zinger et al.
2010/0137827 A1 6/2010 Warren et al.
2010/0160889 A1 6/2010 Smith et al.
2010/0168664 A1 7/2010 Zinger et al.
2010/0168712 A1 7/2010 Tuckwell et al.
2010/0179506 A1* 7/2010 Shemesh ............... A61J 1/2096 604/414
2010/0198148 A1 8/2010 Zinger et al.
2010/0204670 A1 8/2010 Kraushaar et al.
2010/0241088 A1 9/2010 Ranalletta et al.
2010/0274184 A1 10/2010 Chun
2010/0286661 A1 11/2010 Raday et al.
2010/0312220 A1 12/2010 Kalitzki
2011/0004143 A1 1/2011 Beiriger et al.
2011/0004184 A1 1/2011 Proksch et al.
2011/0044850 A1 2/2011 Solomon et al.
2011/0054440 A1 3/2011 Lewis
2011/0087164 A1 4/2011 Mosler et al.
2011/0160701 A1 6/2011 Wyatt et al.
2011/0172636 A1 7/2011 Aasmul
2011/0175347 A1 7/2011 Okiyama
2011/0218511 A1 9/2011 Yokoyama
2011/0224640 A1 9/2011 Kuhn et al.
2011/0230856 A1 9/2011 Kyle et al.
2011/0264037 A1 10/2011 Foshee et al.
2011/0264069 A1 10/2011 Bochenko
2011/0276007 A1 11/2011 Denenburg
2011/0319827 A1 12/2011 Leinsing et al.
2012/0022469 A1 1/2012 Alpert
2012/0053555 A1 3/2012 Ariagno et al.
2012/0059346 A1 3/2012 Sheppard et al.
2012/0067429 A1 3/2012 Mosler et al.
2012/0078214 A1 3/2012 Finke et al.
2012/0123382 A1 5/2012 Kubo
2012/0184938 A1 7/2012 Lev et al.
2012/0215182 A1 8/2012 Mansour et al.
2012/0220977 A1 8/2012 Yaw
2012/0220978 A1 8/2012 Lev et al.
2012/0265163 A1 10/2012 Cheng et al.
2012/0271229 A1 10/2012 Lev et al.
2012/0296307 A1 11/2012 Holt et al.
2012/0310203 A1 12/2012 Khaled et al.
2012/0323172 A1 12/2012 Lev et al.
2012/0323187 A1 12/2012 Iwase et al.
2012/0323210 A1 12/2012 Lev et al.
2013/0046269 A1 2/2013 Lev et al.
2013/0053814 A1 2/2013 Mueller-Beckhaus et al.
2013/0096493 A1 4/2013 Kubo et al.
2013/0144248 A1 6/2013 Putter et al.
2013/0199669 A1 8/2013 Moy et al.
2013/0226100 A1 8/2013 Lev
2013/0231630 A1 9/2013 Kraus et al.
2013/0237904 A1 9/2013 Deneburg et al.
2013/0253448 A1 9/2013 Baron et al.
2013/0289530 A1 10/2013 Wyatt et al.
2014/0020793 A1 1/2014 Denenburg et al.
2014/0096862 A1 4/2014 Aneas
2014/0150911 A1 6/2014 Hanner et al.
2014/0221940 A1 8/2014 Clauson et al.
2014/0277052 A1 9/2014 Haselby et al.
2014/0352845 A1 12/2014 Lev et al.
2015/0082746 A1 3/2015 Ivosevic et al.
2015/0088078 A1 3/2015 Lev et al.

(56) References Cited

U.S. PATENT DOCUMENTS

| | | | |
|---|---|---|---|
| 2015/0290390 | A1 | 10/2015 | Ring et al. |
| 2015/0305770 | A1 | 10/2015 | Fill et al. |
| 2016/0088995 | A1 | 3/2016 | Ueda et al. |

FOREIGN PATENT DOCUMENTS

| | | | |
|---|---|---|---|
| DE | 4122476 | A1 | 1/1993 |
| DE | 19504413 | A1 | 8/1996 |
| DE | 202004012714 | U1 | 11/2004 |
| DE | 202009011019 | U1 | 12/2010 |
| EP | 0192661 | A1 | 9/1986 |
| EP | 0195018 | A1 | 9/1986 |
| EP | 0258913 | A2 | 3/1988 |
| EP | 0416454 | A2 | 3/1991 |
| EP | 0282545 | B1 | 2/1992 |
| EP | 0518397 | A1 | 12/1992 |
| EP | 0521460 | A1 | 1/1993 |
| EP | 0598918 | A1 | 6/1994 |
| EP | 0637443 | A1 | 2/1995 |
| EP | 0737467 | A1 | 10/1996 |
| EP | 761562 | A1 | 3/1997 |
| EP | 765652 | A1 | 4/1997 |
| EP | 765853 | A1 | 4/1997 |
| EP | 0806597 | A1 | 11/1997 |
| EP | 0814866 | A1 | 1/1998 |
| EP | 829248 | A2 | 3/1998 |
| EP | 0856331 | A2 | 8/1998 |
| EP | 882441 | A2 | 12/1998 |
| EP | 0887085 | A2 | 12/1998 |
| EP | 897708 | A2 | 2/1999 |
| EP | 0898951 | A2 | 3/1999 |
| EP | 960616 | A2 | 12/1999 |
| EP | 1008337 | A1 | 6/2000 |
| EP | 1029526 | A1 | 8/2000 |
| EP | 1034809 | A1 | 9/2000 |
| EP | 1051988 | A2 | 11/2000 |
| EP | 1323403 | A1 | 7/2003 |
| EP | 1329210 | A1 | 7/2003 |
| EP | 1396250 | A1 | 3/2004 |
| EP | 1454609 | A1 | 9/2004 |
| EP | 1454650 | A1 | 9/2004 |
| EP | 1498097 | A2 | 1/2005 |
| EP | 1872824 | A1 | 1/2008 |
| EP | 1911432 | A1 | 4/2008 |
| EP | 1919432 | A1 | 5/2008 |
| EP | 1930038 | A2 | 6/2008 |
| EP | 2090278 | A1 | 8/2009 |
| EP | 2351548 | A1 | 8/2011 |
| EP | 2351549 | A1 | 8/2011 |
| EP | 2462913 | A1 | 6/2012 |
| EP | 2512399 | A1 | 10/2012 |
| FR | 2029242 | A5 | 10/1970 |
| FR | 2856660 | A1 | 12/2004 |
| FR | 2869795 | A1 | 11/2005 |
| FR | 2931363 | A1 | 11/2009 |
| GB | 1444210 | A | 7/1976 |
| IL | 171662 | | 10/2005 |
| JP | 03-062426 | B | 9/1991 |
| JP | 4329954 | A | 11/1992 |
| JP | 06-050656 | U | 7/1994 |
| JP | H08-000710 | A | 1/1996 |
| JP | 09-104460 | A | 4/1997 |
| JP | 09-104461 | A | 4/1997 |
| JP | 10-118158 | A | 5/1998 |
| JP | H10-504736 | A | 5/1998 |
| JP | 11503627 | T | 3/1999 |
| JP | 11-319031 | A | 11/1999 |
| JP | 2000-508934 | A | 7/2000 |
| JP | 2000-237278 | A | 9/2000 |
| JP | 2000262497 | A | 9/2000 |
| JP | 2001-505083 | A | 4/2001 |
| JP | 2002-035140 | A | 2/2002 |
| JP | 2002-516160 | A | 6/2002 |
| JP | 2002-355318 | A | 12/2002 |
| JP | 2003-033441 | A | 2/2003 |
| JP | 2003-102807 | A | 4/2003 |
| JP | 2004-097253 | A | 4/2004 |
| JP | 2004-522541 | A | 7/2004 |
| JP | 200661421 | A | 3/2006 |
| JP | 2010-179128 | A | 8/2010 |
| JP | 2012-205769 | A | 10/2012 |
| WO | 8601712 | A1 | 3/1986 |
| WO | 8605683 | A1 | 10/1986 |
| WO | 9003536 | A1 | 4/1990 |
| WO | 9403373 | A1 | 2/1994 |
| WO | 9507066 | A1 | 3/1995 |
| WO | 9600053 | A1 | 1/1996 |
| WO | 9629113 | A1 | 9/1996 |
| WO | 9736636 | A1 | 10/1997 |
| WO | 9832411 | A1 | 7/1998 |
| WO | 9837854 | A1 | 9/1998 |
| WO | 9961093 | A1 | 12/1999 |
| WO | 0128490 | A1 | 4/2001 |
| WO | 0130425 | A1 | 5/2001 |
| WO | 0132524 | A1 | 5/2001 |
| WO | 0160311 | A1 | 8/2001 |
| WO | 0191693 | A2 | 12/2001 |
| WO | 200209797 | A1 | 2/2002 |
| WO | 0232372 | A1 | 4/2002 |
| WO | 0236191 | A2 | 5/2002 |
| WO | 02066100 | A2 | 8/2002 |
| WO | 02089900 | A1 | 11/2002 |
| WO | 03051423 | A2 | 6/2003 |
| WO | 03070147 | A2 | 8/2003 |
| WO | 03079956 | A1 | 10/2003 |
| WO | 2004041148 | A1 | 5/2004 |
| WO | 2005002492 | A1 | 1/2005 |
| WO | 2005041846 | A2 | 5/2005 |
| WO | 2005105014 | A2 | 11/2005 |
| WO | 2006099441 | A2 | 9/2006 |
| WO | 2007015233 | A1 | 2/2007 |
| WO | 2007017868 | A1 | 2/2007 |
| WO | 2007052252 | A1 | 5/2007 |
| WO | 2007101772 | A1 | 9/2007 |
| WO | 2007105221 | A1 | 9/2007 |
| WO | 2008081424 | A2 | 7/2008 |
| WO | 2008126090 | A1 | 10/2008 |
| WO | 2009026443 | A2 | 2/2009 |
| WO | 2009029010 | A1 | 3/2009 |
| WO | 2009038860 | A2 | 3/2009 |
| WO | 2009040804 | A2 | 4/2009 |
| WO | 2009087572 | A1 | 7/2009 |
| WO | 2009093249 | A1 | 7/2009 |
| WO | 2009112489 | A1 | 9/2009 |
| WO | 2009146088 | A1 | 12/2009 |
| WO | 2010061743 | A1 | 6/2010 |
| WO | 2010117580 | A1 | 10/2010 |
| WO | 2011004360 | A1 | 1/2011 |
| WO | 2011039747 | A1 | 4/2011 |
| WO | 2011058545 | A1 | 5/2011 |
| WO | 2011058548 | A1 | 5/2011 |
| WO | 2011077434 | A1 | 6/2011 |
| WO | 2011104711 | A1 | 9/2011 |
| WO | 2012004784 | A1 | 1/2012 |
| WO | 2012063230 | A1 | 5/2012 |
| WO | 2012143921 | A1 | 10/2012 |
| WO | 2012150587 | A1 | 11/2012 |
| WO | 2013127813 | A1 | 9/2013 |
| WO | 2013134246 | A1 | 9/2013 |
| WO | 2013156944 | A1 | 10/2013 |
| WO | 2013156994 | A1 | 10/2013 |
| WO | 2014033706 | A2 | 3/2014 |
| WO | 2014033710 | A1 | 3/2014 |

OTHER PUBLICATIONS

Int'l Search Report dated Feb. 3, 2011 in Int'l Application No. PCT/IL2010/000777; Written Opinion.

Int'l Search Report dated Mar. 17, 2011 in Int'l Application No. PCT/IL2010/000854; Written Opinion.

Int'l Search Report dated Mar. 17, 2011 in Int'l Application No. PCT/IL2010/000915; Written Opinion.

U.S. Appl. No. 13/505,790 by Lev, filed May 3, 2012.

(56) References Cited

OTHER PUBLICATIONS

U.S. Appl. No. 13/505,881 by Lev, filed May 3, 2012.
U.S. Appl. No. 13/522,410 by Lev, filed Jul. 16, 2012.
U.S. Appl. No. 13/576,461 by Lev, filed Aug. 1, 2012.
Office Action dated Jun. 14, 2012 in U.S. Appl. No. 29/376,980.
Office Action dated Jun. 15, 2012 in U.S. Appl. No. 29/413,170.
Office Action dated Jun. 21, 2012 in U.S. Appl. No. 12/596,167.
Alaris Medical Systems Product Brochure, 4 pages, Issue 1, Oct. 11, 1999.
Smart Site Needle-Free Systems, Alaris Medical Systems Webpage, 4 pages, Feb. 2006.
Photographs of Alaris Medical Systems SmartSite.RTM. device, 5 pages, 2002.
Non-Vented Vial Access Pin with ultrasite.rtm. Valve, B. Braun Medical, Inc. website and product description, 3 pages, Feb. 2006. and product description, 3 pages, Feb. 2006.
Int'l Search Report dated Aug. 16, 2012 in Int'l Application No. PCT/IL2012/000164.
U.S. Appl. No. 29/438,134 by Lev, filed Nov. 27, 2012.
U.S. Appl. No. 29/438,141 by Gilboa, filed Nov. 27, 2012.
Int'l Search Report dated Jan. 22, 2013 in Int'l Application No. PCT/IL2012/000354.
Int'l Search Report dated Mar. 18, 2013 in Int'l Application No. PCT/IL2012/050516.
Office Action dated Apr. 2, 2013 in U.S. Appl. No. 13/505,790.
Int'l Search Report and Written Opinion dated Mar. 6, 2012 in Int'l Application No. PCT/IL2011/000834.
U.S. Appl. No. 13/883,289 by Lev, filed May 3, 2013.
Int'l Search Report & Written Opinion dated Mar. 7, 2012 in Int'l Application No. PCT/IL2011/000829.
U.S. Appl. No. 13/884,981 by Denenburg, filed May 13, 2013.
Office Action dated May 31, 2013 in U.S. Appl. No. 13/505,790.
Int'l Search Report dated Jun. 5, 2013 in Int'l Application No. PCT/IL2012/050407.
Int'l Search Report dated Jun. 19, 2013 in Int'l Application No. PCT/IL2013/050167.
Int'l Search Report dated Jul. 1, 2013 in Int'l Application No. PCT/IL2013/050180.
Int'l Search Report dated Jul. 31, 2013 in Int'l Application No. PCT/IL2013/050313.
Int'l Search Report dated Jul. 26, 2013 in Int'l Application No. PCT/IL2013/050316.
English translation of an Office Action dated Jun. 19, 2013 in JP Application No. 2012-531551.
Office Action dated Aug. 20, 2013 in U.S. Appl. No. 13/576,461 by Lev.
Int'l Preliminary Report on Patentability dated Aug. 28, 2012 in Int'l Application No. PCT/IL2011/000186.
U.S. Appl. No. 14/005,751 by Denenburg, filed Sep. 17, 2013.
English translation of an Office Action dated Jul. 26, 2013 in JP Application No. 2012-538464.
International Search Report dated Jan. 23, 2007 in Int'l Application No. PCT/IL/2006/001228.
IV disposables sets catalogue, Cardinal Health, Alaris® products, SmartSite® access devices and accessories product No. 10013365, SmartSite add-on bag access device with spike adapter and needle-free valve bag access port, pp. 1-5, Fall edition (2007).
Drug Administration Systems product information sheets; http://www.westpharma.com/eu/en/products/Pages/Vial2Bag.aspx; pp. 1-3 (admitted prior art).
Office Action dated Jun. 8, 2010 in U.S. Appl. No. 12/112,490 by Zinger.
Office Action dated Sep. 28, 2010 in U.S. Appl. No. 12/112,490 by Zinger.
Article with picture of West Pharmaceutical Services' Vial2Bag Needleless System, [on-line]; ISIPS Newsletter, Oct. 26, 2007]; retrieved from Internet Feb. 16, 2010]; URL:<http://www.isips.org/reports/ISIPS_Newsletter_October_26_2007. html.> (7 pages. see pp. 5-6).
Office Action dated Jun. 15, 2011 in JP Application No. 2008-538492.
Translation of Office Action dated Jun. 18, 2012 in JP Application No. 2008-538492.
Translation of Office Action dated Apr. 15, 2013 in JP Application No. 2008-538492.
Office Action dated Jul. 13, 2012 in U.S. Appl. No. 12/112,490 by Zinger.
Office Action dated Jan. 23, 2013 in U.S. Appl. No. 12/112,490 by Zinger.
Int'l Preliminary Report on Patentability dated May 6, 2008 in Int'l Application No. PCT/IL2006/001228.
Written Opinion dated Aug. 16, 2012 in Int'l Application No. PCT/IL2012/000164.
English translation of an Office Action dated Sep. 10, 2013 in JP Application No. 2012-554468.
Office Action dated Nov. 11, 2013 in IL Application No. 218730.
U.S. Appl. No. 29/478,723 by Lev, filed Jan. 8, 2014.
U.S. Appl. No. 29/478,726 by Lev, filed Jan. 8, 2014.
Office Action dated Jan. 2, 2014 in U.S. Appl. No. 13/505,881 by Lev.
Int'l Preliminary Report on Patentability dated Sep. 24, 2013 in Int'l Application No. PCT/IL2012/000354.
Office Action dated Feb. 13, 2014 in U.S. Appl. No. 13/884,981 by Denenburg.
U.S. Appl. No. 14/345,094 by Lev, filed Mar. 14, 2014.
Int'l Search Report and Written Opinion dated Jan. 7, 2014 in Int'l Application No. PCT/IL2012/050721.
English translation of an Office Action dated Jan. 9, 2014 in JP Application No. 2010-526421.
English translation of an Office Action dated Dec. 4, 2013 in CN Application No. 201080051210.3.
English translation of an Office Action issued Dec. 25, 2013 in CN Application No. 201180006530.1.
Office Action dated Nov. 28, 2013 in IN Application No. 4348/DELNP/2008.
Office Action dated Oct. 8, 2013 in CN Application No. 201080043825.1.
English translation of an Office Action dated Feb. 4, 2014 in JP Application No. 2012-554468.
Office Action dated Jan. 17, 2014 in CN Application No. 201180006534.X.
Int'l Search Report and Written Opinion dated May 8, 2014 in Int'l Application No. PCT/IL2013/050706.
English translation of an Office Action dated Apr. 28, 2014 in JP Application No. 2013-537257.
Int'l Preliminary Report on Patentability dated Jan. 14, 2014 in Int'l Application No. PCT/IL2012/050516.
Office Action dated May 6, 2014 in U.S. Appl. No. 13/505,881 by Lev.
U.S. Appl. No. 14/366,306 by Lev, filed Jun. 18, 2014.
Office Action dated Apr. 17, 2014 in CN Application No. 201080051201.4.
Int'l Search Report and Written Opinion dated Jul. 16, 2014 in Int'l Application No. PCT/IL2014/050327.
English translation of an Office Action dated Jun. 30, 2014 in CN Application No. 201180052962.6.
Extended European Search Report dated Jun. 3, 2014 in EP Application No. 08781828.2.
Written Opinion dated Jul. 1, 2013 in Int'l Application No. PCT/IL2013/050180.
Int'l Preliminary Report on Patentability dated Apr. 1, 2014 in Int'l Application No. PCT/IL2013/050180.
Written Opinion dated Jul. 31, 2013 in Int'l Application No. PCT/IL2013/050313.
Int'l Preliminary Report on Patentability dated May 12, 2014 in Int'l Application No. PCT/IL2013/050316.
Office Action dated Jul. 31, 2014 in U.S. Appl. No. 29/438,141 by Gilboa.
U.S. Appl. No. 14/385,212 by Lev, filed Sep. 15, 2014.
U.S. Appl. No. 29/502,037 by Lev, filed Sep. 11, 2014.
U.S. Appl. No. 29/502,053 by Lev, filed Sep. 11, 2014.
U.S. Appl. No. 14/391,792 by Lev, filed Oct. 10, 2014.

(56) References Cited

OTHER PUBLICATIONS

U.S. Appl. No. 14/504,979 by Lev, filed Oct. 2, 2014.
Int'l Search Report and Written Opinion dated Sep. 2, 2014 in Int'l Application No. PCT/IL2014/050405.
Int'l Search Report and Written Opinion dated Oct. 17, 2014 in Int'l Application No. PCT/IL2014/050680.
English translation of an Office Action dated Aug. 28, 2014 in JP Application No. 2013-168885.
Grifols Vial Adapter Product Literature, 2 pages, Jan. 2002.
Novel Transfer, Mixing and Drug Delivery Systems, MOP Medimop Medical Projects Ltd. Catalog, 4 pages, Rev. 4, 2004.
Office Action dated Oct. 6, 2003 in U.S. Appl. No. 10/062,796.
Office Action dated Feb. 22, 2005 in U.S. Appl. No. 10/062,796.
Office Action dated Oct. 5, 2005 in U.S. Appl. No. 10/062,796.
Office Action dated Feb. 20, 2009 in U.S. Appl. No. 11/694,297.
Int'l Search Report dated Dec. 6, 2006 in Int'l Application No. PCT/IL2006/000912.
Int'l Preliminary Report on Patentability dated Dec. 4, 2007 in Int'l Application No. PCT/IL2006/000912.
http://www.westpharma.com/en/products/Pages/Mixject.aspx (admitted prior art).
http://www.westpharma.com/SiteCollectionDocuments/Recon/mixject%20product%20sheet.pdf; Mixject product information sheet pp. 1. (admitted prior art).
Int'l Search Report dated Jul. 27, 2007 in Int'l Application No. PCT/IL2007/000343.
Int'l Preliminary Report on Patentability dated Jun. 19, 2008 in Int'l Application No. PCT/IL2007/000343.
Int'l Search Report dated Mar. 27, 2009 in Int'l Application No. PCT/U52008/070024.
Int'l Search Report dated Oct. 17, 2005 in Int'l Application No. PCT/IL2005/000376.
Int'l Preliminary Report on Patentability dated Jun. 19, 2006 in Int'l Application No. PCT/IL2005/000376.
Written Opinion of ISR dated Jun. 19, 2006 in Int'l Application No. PCT/IL2005/000376.
Int'l Search Report dated Aug. 25, 2008 in Int'l Application No. PCT/IL2008/000517.
Written Opinion of the ISR dated Oct. 17, 2009 in Int'l Application No. PCT/IL08/00517.
Int'l Preliminary Report on Patenability dated Oct. 20, 2009 in Int'l Application No. PCT/IL2008/000517.
Written Opinion of the Int'l Searching Authority dated Oct. 27, 2008 in Int'l Application No. PCT/US2008/070024.
Int'l Search Report dated Mar. 12, 2009 in Int'l Application No. PCT/IL2008/001278.
Office Action dated Jan. 20, 2010 in JP Application No. 2007-510229.
Office Action dated Apr. 20, 2010 in U.S. Appl. No. 11/997,569.
Int'l Search Report dated Nov. 20, 2006 in Int'l Application No. PCT/IL2006/000881.
Office Action dated May 27, 2010 in U.S. Appl. No. 11/559,152.
Decision to Grant dated Apr. 12, 2010 in EP Application No. 08738307.1.
Office Action dated Jun. 1, 2010 in U.S. Appl. No. 11/568,421.
Office Action dated Nov. 12, 2010 in U.S. Appl. No. 29/334,697.
The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).
Publication date of Israeli Patent Application 186290 [on-line]. ]Retrieved from Internet May 24, 2010]. URL:<http://www.ilpatsearch.justrice.govil/UI/RequestsList.aspx>. (1 page).
Int'l Search Report dated Nov. 25, 2010 in Int'l Application No. PCT/IL2010/000530.
Office Action dated Feb. 7, 2011 in U.S. Appl. No. 12/783,194.
Office Action dated Dec. 20, 2010 in U.S. Appl. No. 12/063,176.
Office Action dated Dec. 13, 2010 in U.S. Appl. No. 12/293,122.
Office Action dated Nov. 29, 2010 in U.S. Appl. No. 11/568,421.
Office Action dated Dec. 23, 2010 in U.S. Appl. No. 29/334,696.
Int'l Search Report dated Mar. 17, 2011 in Int'l Application No. PCT/IL2010/000854.
Overview—Silicone Rubber [retrieved from http://www.knovel.com/web/portal/browse/display?_EXT_KNOVEL_DISPLAY_bookid=1023&VerticalID=0 on Feb. 9, 2011].
Int'l Search Report dated Mar. 17, 2011 in Int'l Application No. PCT/IL2010/00915.
Office Action dated May 12, 2011 in U.S. Appl. No. 12/063,176.
Office Action dated Jul. 11, 2011 in U.S. Appl. No. 12/293,122.
Int'l Search Report dated Jul. 12, 2011 in Int'l Application No. PCT/IL2011/000187.
Int'l Search Report dated Jul. 12, 2011 in Int'l Application No. PCT/IL2011/000186.
Office Action dated Aug. 3, 2011 in JP Application No. 2008-525719.
Int'l Search Report dated Oct. 7, 2011 in Int'l Application No. PCT/IL2011/000511.
Int'l Search Report dated Mar. 6, 2012 in Int'l Application No. PCT/IL2011/000834; Written Opinion.
Office Action dated Mar. 1, 2012 in JP Application No. 2007-510229.
Int'l Search Report dated Mar. 7, 2012 in Int'l Application No. PCT/IL2011/000829; Written Opinion.
Office Action dated Mar. 13, 2012 in CA Application No. 2,563,643.
Office Action dated Mar. 1, 2012 in CN Application No. 2008801108283.4.
Office Action dated Mar. 28, 2016 in JP Application No. 2016-507113.
Notice of Allowance dated Mar. 17, 2016 in U.S. Appl. No. 29/502,037 by Lev.
Office Action dated Mar. 25, 2016 in U.S. Appl. No. 29/478,726 by Lev.
Office Action dated Dec. 9, 2015 in U.S. Appl. No. 29/478,723 by Lev.
West, Vial2Bag DC system, Oct. 2, 2014, https://web.archive.org/web/20141002065133/http://www.westpharma.com/en/products/Pages/Reconstitutionsystems.aspx.
Youtube.com, Vial2Bag DC, Aug. 21, 2014, https://www.youtube.com/watch?v=FEOkglxNBrs.
Office Action dated Dec. 9, 2015 in U.S. Appl. No. 29/478,726 by Lev.
Notice of Allowance dated Jan. 12, 2016 in U.S. Appl. No. 14/385,212 by Lev.
Written Opinion dated Apr. 10, 2015 in Int'l Application No. PCT/IL2014/050405.
Response to Written Opinion dated Mar. 9, 2015 in Int'l Application No. PCT/IL2014/050405.
Int'l Preliminary Report on Patentability dated Aug. 24, 2015 in Int'l Application No. PCT/IL2014/050405.
U.S. Appl. No. 14/888,590 by Marks, filed Nov. 2, 2015.
U.S. Appl. No. 14/784,300 by Lev, filed Oct. 14, 2015.
Office Action dated Oct. 5, 2015 in U.S. Appl. No. 14/385,212 by Lev.
U.S. Appl. No. 29/544,969 by Ben Shalom, filed Nov. 9, 2015.
Office Action dated Aug. 24, 2015 in U.S. Appl. No. 14/366,306 by Lev.
Office Action dated Mar. 10, 2015 in EP Application No. 12 812 395.7.
Office Action dated Aug. 7, 2015 in JP Application No. 2015-529206.
Written Opinion dated Jun. 5, 2013 in Int'l Application No. PCT/IL2012/050407.
Int'l Preliminary Report on Patentability dated Aug. 20, 2014 in Int'l Application No. PCT/IL2012/050407.
Office Action dated Jan. 2, 2015 in U.S. Appl. No. 29/438,141 by Gilboa.
Office Action dated Jan. 5, 2015 in U.S. Appl. No. 29/413,220 by Lev.
Office Action dated Jan. 7, 2015 in U.S. Appl. No. 29/438,134 by Lev.
U.S. Appl. No. 14/423,612 by Lev, filed Feb. 24, 2015.
U.S. Appl. No. 14/425,582 by Lev, filed Mar. 3, 2015.

(56) References Cited

OTHER PUBLICATIONS

Office Action dated Mar. 17, 2015 in U.S. Appl. No. 14/504,979 by Lev.
Office Action dated Apr. 9, 2015 in U.S. Appl. No. 13/883,289 by Lev.
Office Action dated May 28, 2015 in U.S. Appl. No. 14/391,792 by Lev.
Office Action dated Dec. 21, 2016 in IL Application No. 228452.
Extended European Search Report dated Feb. 16, 2017 in EP Application No. 16200458.
Int'l Search Report and Written Opinion dated Sep. 14, 2016 in Int'l Application No. PCT/IL2016/050709.
Int'l Search Report and Written Opinion dated Oct. 11, 2016 in Int'l Application No. PCT/IL2016/050782.
Vial-Mate Adapter Device, Baxter, May 2017, downloaded from web page:http://www.baxtermedicationdeliveryproducts.com/drug-delivery/vialmate.html, Download Date: Jul. 28, 2017, original posting ate: unknown, 1page.

* cited by examiner

D11=6.5MM
D12=7.5MM
H11=7.5MM
D13=10.5MM

LIQUID DRUG TRANSFER DEVICES

CROSS-REFERENCE TO RELATED APPLICATION

This application is a Section 371 of International Application No. PCT/IL2013/050706, filed Aug. 20, 2013, which was published in the English language on Mar. 6, 2014, under International Publication No. WO 2014/033706 A3, which claims priority to U.S. Provisional Application No. 61/731,574 filed Nov. 30, 2012, and the disclosure of which is incorporated herein by reference.

FIELD OF THE INVENTION

The invention relates to liquid drug transfer devices.

BACKGROUND OF THE INVENTION

Liquid drug transfer devices including universal drug vial adapters for telescopic mounting on a drug vial of a small drug vial and a large drug vial can be classified into one of two types as follows:

First, a universal drug vial adapter shaped and dimensioned to telescopically clamp equally on a small drug vial and a large drug vial. Exemplary prior art references include inter alia U.S. Pat. No. 5,334,179 to Poli et al, U.S. Pat. No. 6,656,433 to Sasso, U.S. Pat. No. 6,875,205 to Leinsing, and U.S. Pat. No. 8,469,939 to Fangrow.

And second, a universal drug vial adapter shaped and dimensioned to telescopically clamp on a large drug vial only and provided with a vial coupling adapter for insertion thereinto shaped and dimensioned to telescopically clamp on a small drug vial only. U.S. Pat. No. 5,893,397 to Peterson et al discloses a Medication Vial/Syringe Liquid Transfer Apparatus including a liquid transfer apparatus (20) with a liquid drug transfer device (24) and a vial coupling adapter (26).

Some liquid drug transfer devices are intended to be mounted on injection ports of infusion bags containing infusion liquid. Different suppliers of infusion bags provide injection ports of different sizes. U.S. Pat. No. 4,607,671 to Aalto et al. discloses a reconstitution device (10) including a plastic housing (52) for sealed mounting on an injection site (34). The plastic housing (34) includes a rigid tubular double pointed needle (54).

There is a need for liquid drug transfer devices with improved universal drug vial adapters for mixing, reconstitution and administration purposes and improved injection port connectors.

SUMMARY OF THE INVENTION

One aspect of the present invention is directed toward liquid drug transfer devices with universal drug vial adapters for telescopic clamping a drug vial of a so-called small drug vial and a so-called large drug vial. Large drug vials have the same shape as small drug vials but proportionally larger dimensions. In particular, large drug vials have a drug vial closure and a drug vial neck with wider diameters than their counterpart small drug vials. For the purpose of the present description, so-called small drug vials are widely commercially available 13 mm drug vials and so-called large drug vials are widely commercially available 20 mm drug vials. The present invention is equally applicable to larger so-called small drug vials and so-called large drug vials containing larger liquid volumes, for example, a 28 mm diameter drug vial closure and a 32 mm diameter drug vial closure, respectively.

Some preferred embodiments of the liquid drug transfer devices in accordance with the present invention include a universal drug vial adapter employing the same at least one pair of generally opposite upright flex members for clamping a small drug vial and a large drug vial by virtue of the inherent flexibility of the plastic material, for example, polycarbonate, and the like, from which the universal drug vial adapters are manufactured. The at least one pair of flex members are resiliently flexibly mounted on crosspieces towards a drug vial base as opposed to a drug vial head on telescopically clamping a universal drug vial adapter on a drug vial. The flex members have flex member free ends opposite their respective crosspieces which each include an inward radial directed drug vial grip. The inward radial directed drug vial grips underlie a drug vial head on telescopically clamping a universal drug vial adapter on a drug vial. Generally speaking, the flex members are outwardly resiliently flexed correspondingly at their crosspieces with respect to the longitudinal drug vial adapter axis to a greater extent on telescopically clamping the universal drug vial adapter on a large drug vial compared to telescopically mounting the universal drug vial adapter on a small drug vial.

Other preferred embodiments of the liquid drug transfer devices in accordance with the present invention include a universal drug vial adapter employing a set of minor flex members for telescopically clamping a small drug vial and a set of major flex members encircling the set of minor flex members for telescopically clamping a large drug vial whereupon the large drug vial underlies the set of minor flex members. The set of major flex members are preferably arranged such that the set of minor flex members are free to outwardly flex with respect to a longitudinal drug vial adapter axis on being telescopically clamped on a small drug vial without interference from the set of major flex members.

A wide range of liquid drug transfer devices can be formed with the universal drug vial adapters of the present invention for different liquid drug transfer purposes. The universal drug vial adapters can be optionally formed in vented and unvented versions. Some liquid drug transfer devices can include an integral access port and an integral puncturing member for puncturing a drug vial stopper on telescopically clamping a drug vial for enabling flow communication with its interior. Such liquid drug transfer devices include inter alia a female drug vial adapter with a female Luer connector, a male drug vial adapter including a male Luer connector, and the like.

Other liquid drug transfer devices can be so-called ready-to-use medical devices including a pre-attached intact, namely, not punctured, drug vial. Such liquid drug transfer devices can include a discrete liquid transfer member with a puncturing member for puncturing a drug vial on actuation. The universal drug vial adapters of the present invention are preferably designed such that an intact drug vial can be readily released by a drug vial release tool for subsequent use, thereby avoiding possible drug waste. Intact drug vials can be possibly returned to suitable storage conditions without a bulky liquid drug transfer device.

Another aspect of the present invention is directed to liquid drug transfer devices with a universal injection port connector for attachment to a conventional injection port of an infusion bag. Conventional injection ports include an injection port tip with a trailing injection port tip rim disposed behind an exposed plug surface of a self-sealing plug for needle injection of syringe contents into an infusion bag. The universal injection port connectors include a multitude of curved connector members which are outwardly urged from their non-flexed position on forced inward insertion of an injection port tip therethrough such that the multitude of curved connector members snap behind the trailing injection port tip rim, thereby precluding sliding withdrawal of the injection port tip from the universal injection port connector. By virtue of their curved shape, the connector members of the universal injection port connector of the present invention are capable of countering a greater withdrawal force compared to straight connector members. Moreover, the curved connector members facilitate mounting on different sizes of injection ports typically of different suppliers of infusion liquid containers.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE INVENTION

Figure 1:
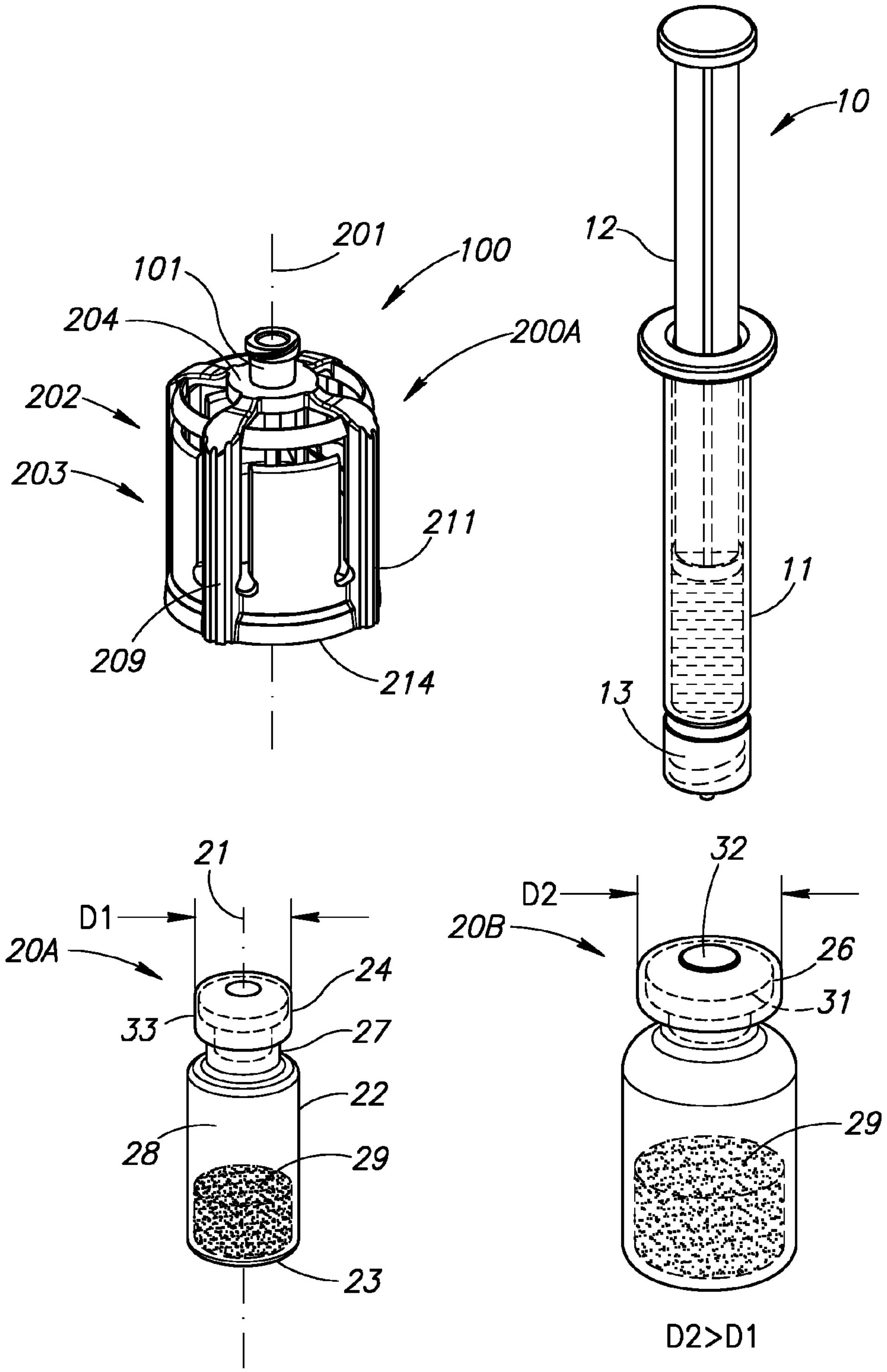
FIG. 1 is a pictorial view of a syringe, a small drug vial, a large drug vial, and a first preferred embodiment of a liquid drug transfer device in accordance with the present invention.
Figure 2:
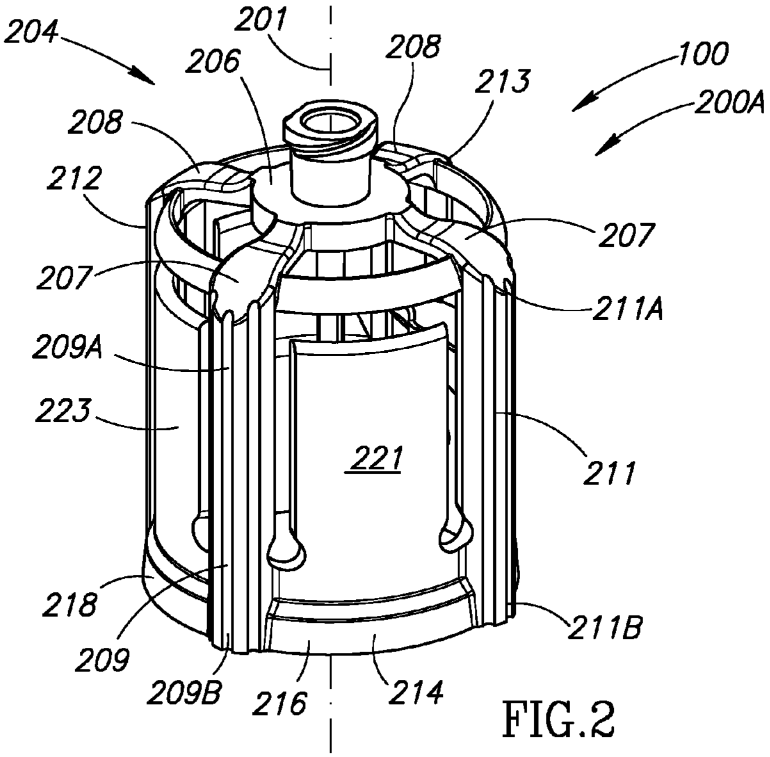
FIG. 2 is a front perspective view of FIG. 1's liquid drug transfer device.
Figure 3:
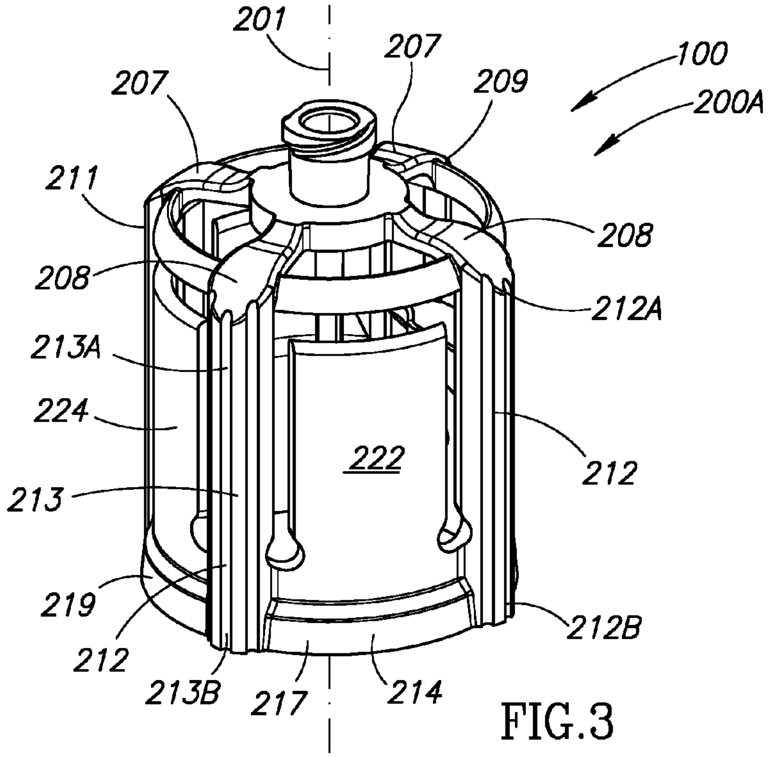
FIG. 3 is a rear perspective view of FIG. 1's liquid drug transfer device.
Figure 4A:
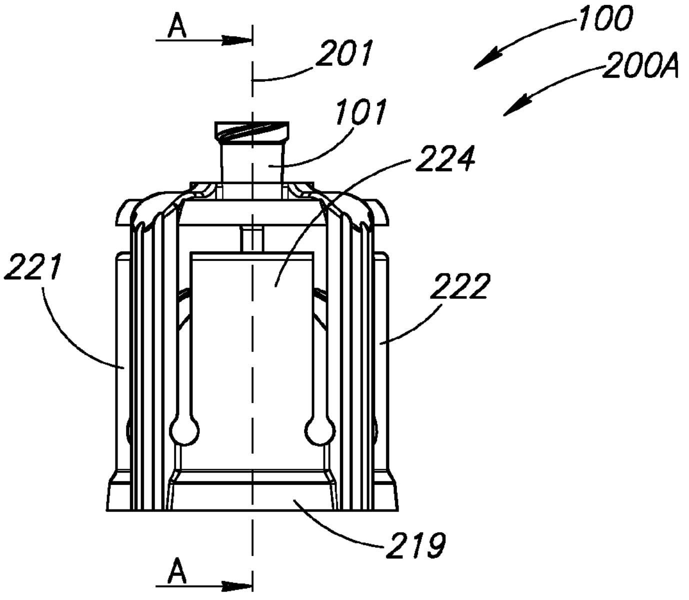
FIG. 4A is a right side elevation view of FIG. 1's liquid drug transfer device.
Figure 4B:
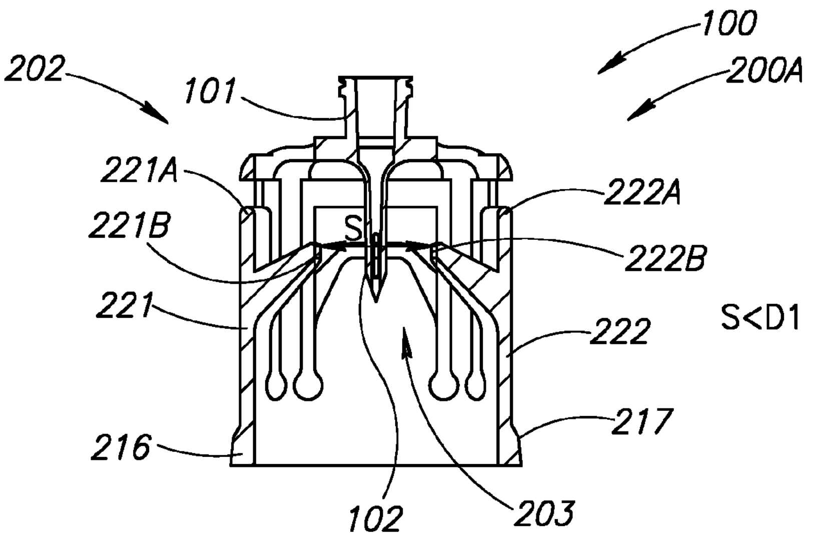
FIG. 4B is a longitudinal cross section of FIG. 1's liquid drug transfer device along line A-A in FIG. 4A.
Figure 5A:
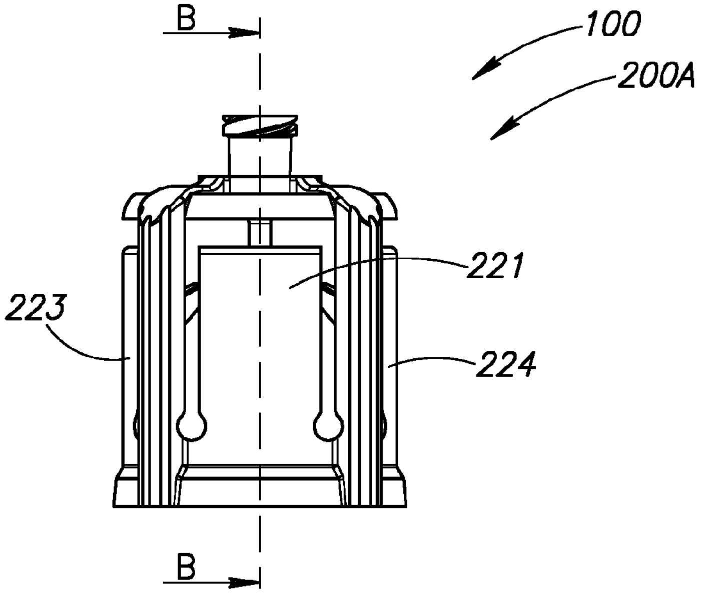
FIG. 5A is a front elevation view of FIG. 1's liquid drug transfer device.
Figure 5B:
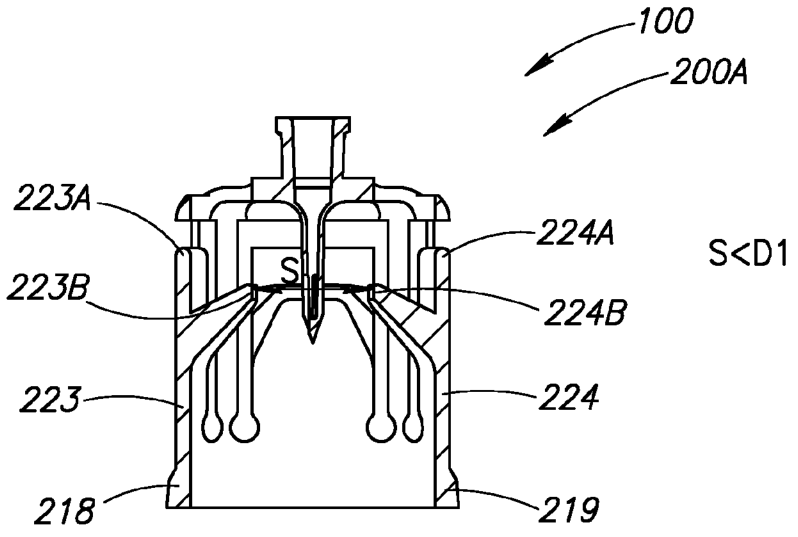
FIG. 5B is a longitudinal cross section of FIG. 1's liquid drug transfer device along line B-B in FIG. 5A.
Figure 6:
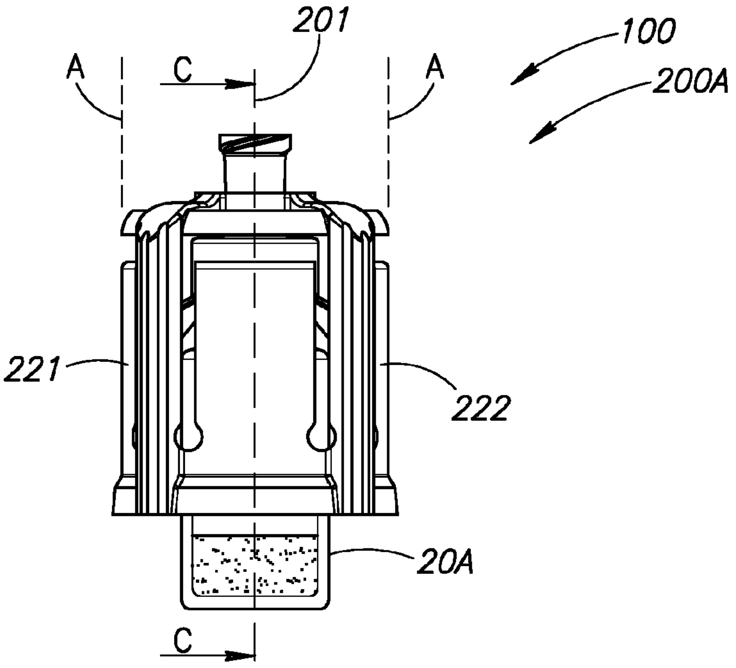
FIG. 6 is a front elevation view of FIG. 1's liquid drug transfer device telescopically clamped on a small drug vial.
Figure 7:
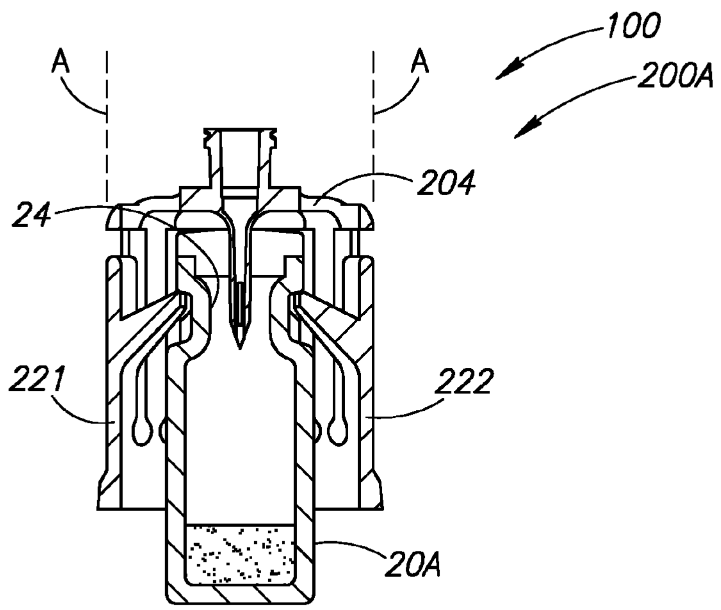
FIG. 7 is a longitudinal cross section of FIG. 6's assemblage along line C-C thereon.
Figure 8:
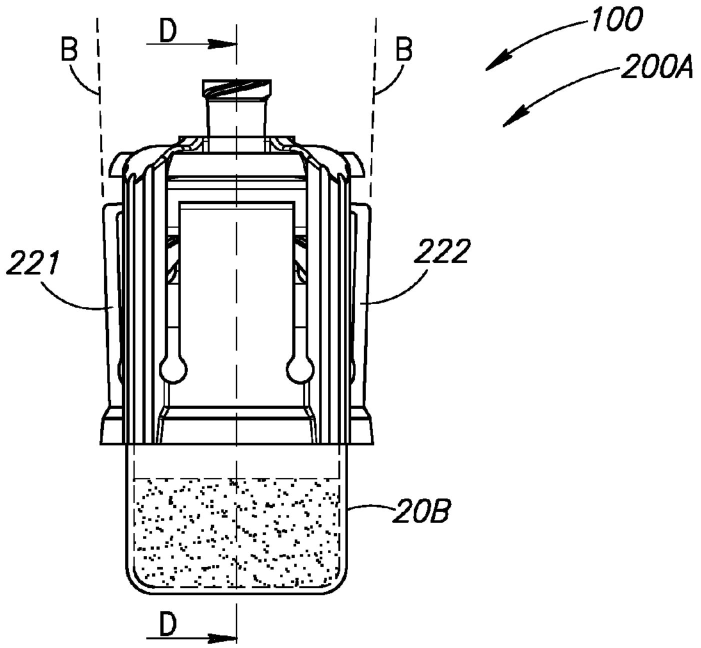
FIG. 8 is a front elevation view of FIG. 1's liquid drug transfer device telescopically clamped on a large drug vial.
Figure 9:
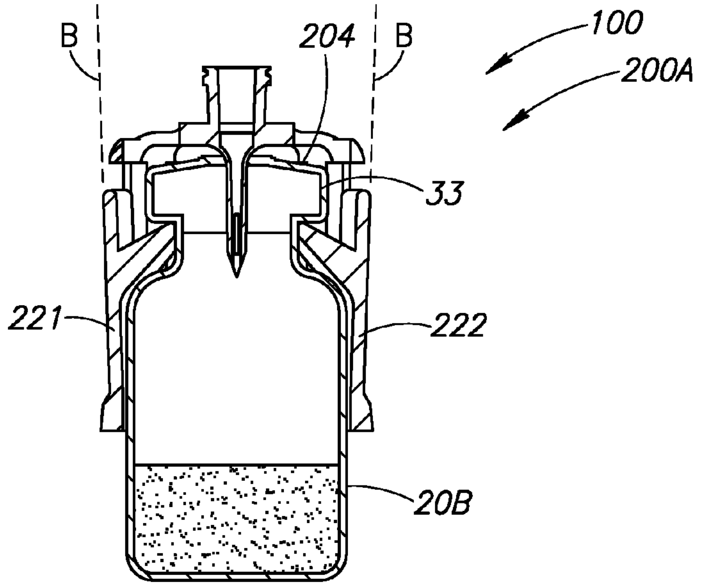
FIG. 9 is a longitudinal cross section of FIG. 8's assemblage along line D-D thereon.

FIG. 1 shows a syringe 10, a small drug vial 20A, a large drug vial 20B, and a liquid drug transfer device 100 constituted as a female vial adapter for use with the syringe 10 and a drug vial 20 of the small drug vial 20A and the large drug vial 20B.

The syringe 10 includes a barrel 11 with a plunger rod 12 and a male Luer lock connector 13. The syringe 10 can be formed with other types of male connectors, for example, a slip Luer connector, and the like. The syringe 10 is typically filled with diluent. Alternatively, the syringe 10 can include an active liquid component.

The drug vials 20 have a longitudinal drug vial axis 21 and include a drug vial body 22 having a drug vial base 23, a drug vial head 24 defining a drug vial opening 26, and a narrow diameter drug vial neck 27 between the drug vial body 22 and the drug vial head 24. The drug vials 20 have a drug vial interior 28 for storing a powder or liquid medicament 29. The drug vials 20 are sealed by a drug vial stopper 31 inserted into the drug vial opening 26. The drug vial stopper 31 has an uppermost drug vial surface 32. The drug vials 20 are hermetically sealed by a drug vial closure 33 constituted, for example, by an aluminum band, and the like.

Widely commercially available small drug vials 20A have a drug vial closure 33 with an external diameter D1 of between 13 mm and 14 mm and widely commercially available large drug vials 20B have a drug vial closure 33 with an external diameter D2>D1 and typically between 20 mm and 21 mm.

FIGS. 1 to 11 show the liquid drug transfer device 100 includes a universal drug vial adapter 200A and a female Luer connector 101 for engagement with the syringe's male Luer lock connector 13. The liquid drug transfer device 100 includes a tubular puncturing member 102 in flow communication with the female Luer connector 101 for enabling flow access to a drug vial interior 28.

The universal drug vial adapter 200A has a longitudinal drug vial adapter axis 201 and a skirt 202 for defining a drug vial cavity 203 for snugly telescopically receiving at least a top part of the drug vial 20B therein and therefore inherently a top part of the drug vial 20A. The skirt 202 includes a top wall 204 constituted by an annular centerpiece 206 with a first pair of two radial directed struts 207 and a second pair of two radial directed struts 208. The annular centerpiece 206 is formed with the upright female Luer connector 101.

The skirt 202 includes a first pair of axial directed spaced apart flex member supports 209 and 211 downward depending from the radial directed struts 207. The skirt 202 includes a second pair of axial directed spaced apart flex member supports 212 and 213 downward depending from the radial directed struts 208. The first pair of axial directed flex member supports 209 and 211 are opposite the second pair of axial directed flex member supports 212 and 213.

The flex member support 209 has a proximate end 209A adjacent the top wall 204 and a distal end 209B remote therefrom. The flex member support 211 has a proximate end 211A adjacent the top wall 204 and a distal end 211B remote therefrom. The flex member support 212 has a proximate end 212A adjacent the top wall 204 and a distal end 212B remote therefrom. The flex member support 213 has a proximate end 213A adjacent the top wall 204 and a distal end 213B remote therefrom.

The skirt 202 includes a single continuous annular support 214 including a first crosspiece 216 extending between the distal ends 209B and 211B, a second crosspiece 217 extending between the distal ends 212B and 213B, a third crosspiece 218 extending between the distal ends 209B and 212B and a fourth crosspiece 219 extending between the distal ends 211B and 213B.

The skirt 202 includes an axial directed first flex member 221 resiliently flexibly mounted on the first crosspiece 216, an axial directed second flex member 222 resiliently flexibly mounted on the second crosspiece 217 and opposite the first flex member 221, an axial directed third flex member 223 resiliently flexibly mounted on the third crosspiece 218 between the first flex member 221 and the second flex member 222, and an axial directed fourth flex member 224 resiliently flexibly mounted on the fourth crosspiece 219 and opposite the third flex member 223.

The first flex member 221 has a first flex member free end 221A remote from the first crosspiece 216 and an inward radial directed first drug vial grip 221B theretoward. The second flex member 222 has a second flex member free end 222A remote from the second crosspiece 217 and an inward radial directed second drug vial grip 222B theretoward. The third flex member 223 has a third flex member free end 223A remote from the third crosspiece 218 and an inward radial directed third drug vial grip 223B theretoward. The fourth flex member 224 has a fourth flex member free end 224A remote from the fourth crosspiece 219 and an inward radial directed fourth drug vial grip 224B theretoward.

The first drug vial grip 221B and the second drug vial grip 222B define a separation S therebetween where S<D1 and similarly the third drug vial grip 223B and the fourth drug vial grip 224B define the separation S therebetween such that they underlie a drug vial closure 33 of a drug vial 20A on telescopically clamping the liquid drug transfer device 100 thereon. Since D2>D1, the drug vial grips 221B, 222B, 223B and 224B also underlie a drug vial closure 33 of a drug vial 20B.

The flex members 221, 222, 223 and 224 are generally parallel to the longitudinal drug vial adapter axis 201 before telescopically clamping the liquid drug transfer device 100 on a drug vial 20A. On telescopically clamping the liquid drug transfer device 100 on a drug vial 20A, the flex members 221, 222, 223 and 224 are outwardly resiliently flexed at their respective crosspieces 216, 217, 218 and 219 with respect to the longitudinal drug vial adapter axis 201 as the drug vial closure 33 passes from beneath the drug vial grips 221B, 222B, 223B and 224B to thereabove under the top wall 204 whereupon the flex members 221, 222, 223 and 224 revert to being generally parallel to the longitudinal drug vial adapter axis 201 as depicted by dashed lines A in FIGS. 6 and 7.

In the case of telescopically clamping the liquid drug transfer device 100 on a drug vial 20B, the flex members 221, 222, 223 and 224 are further outwardly resiliently flexed at their respective crosspieces 216, 217, 218 and 219 with respect to the longitudinal drug vial adapter axis 201 relative to the drug vial 20A due to the former 20B have a wide diameter drug vial closure 33 than the latter 20A. In the case of the drug vial 20B, the flex members 221, 222, 223 and 224 are prevented from fully reverting to being generally parallel to the longitudinal drug vial adapter axis 201 but rather remain outwardly flexed with respect to their original unflexed position as depicted by dashed lines B in FIGS. 8 and 9.

Figure 10:
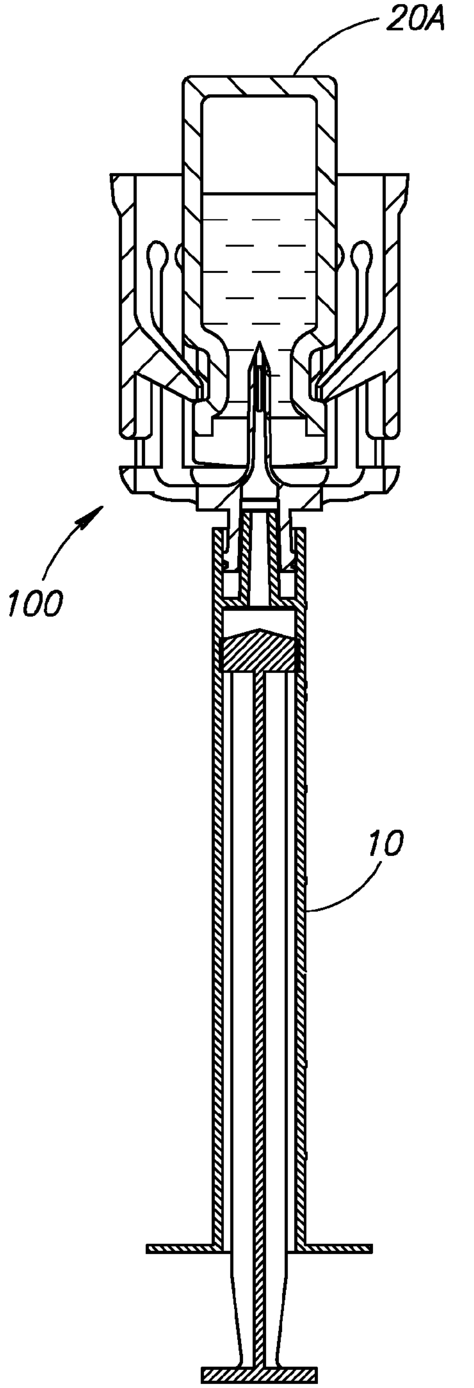
FIG. 10 is a pictorial view showing syringe aspiration of liquid contents from FIG. 6's assemblage.

FIG. 10 shows a syringe 10 attached to the liquid drug transfer device 100 mounted on a drug vial 20A for mixing, reconstitution and aspiration purposes.

Figure 11:
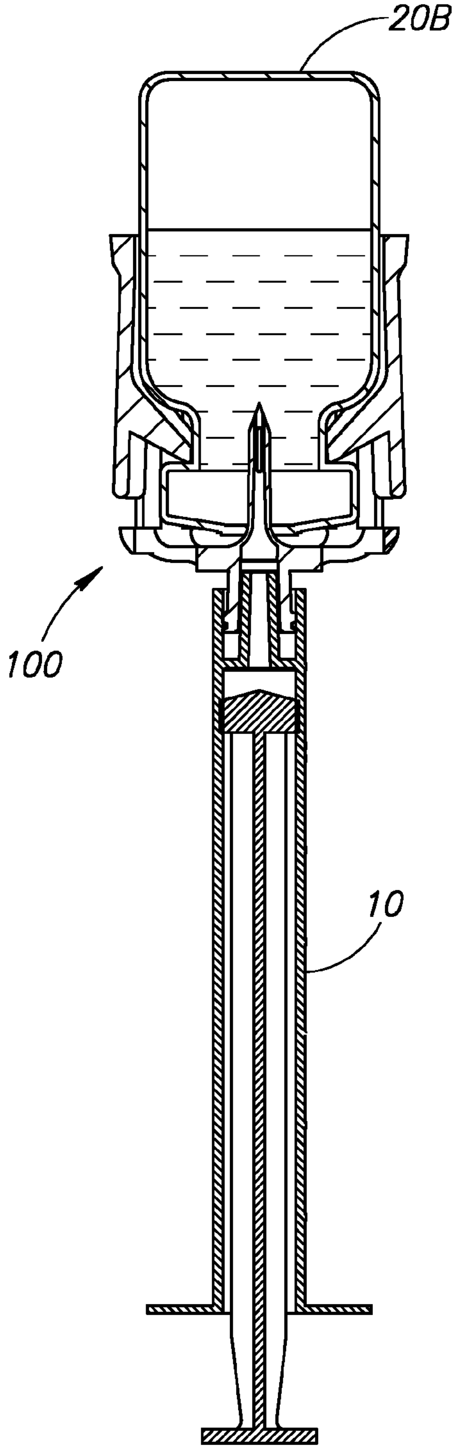
FIG. 11 is a pictorial view showing syringe aspiration of liquid contents from FIG. 8's assemblage.

FIG. 11 shows a syringe 10 attached to the liquid drug transfer device 100 mounted on a drug vial 20B for mixing, reconstitution and aspiration purposes.

Figure 12:
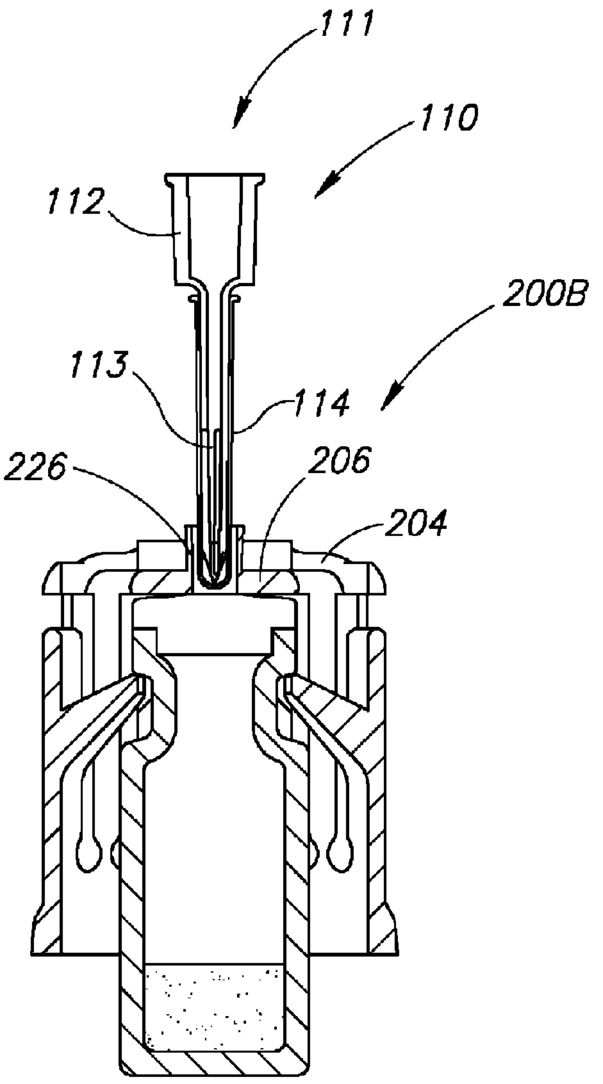
FIG. 12 is a longitudinal cross section of a second preferred embodiment of a liquid drug transfer device in accordance with the present invention.
Figure 13:
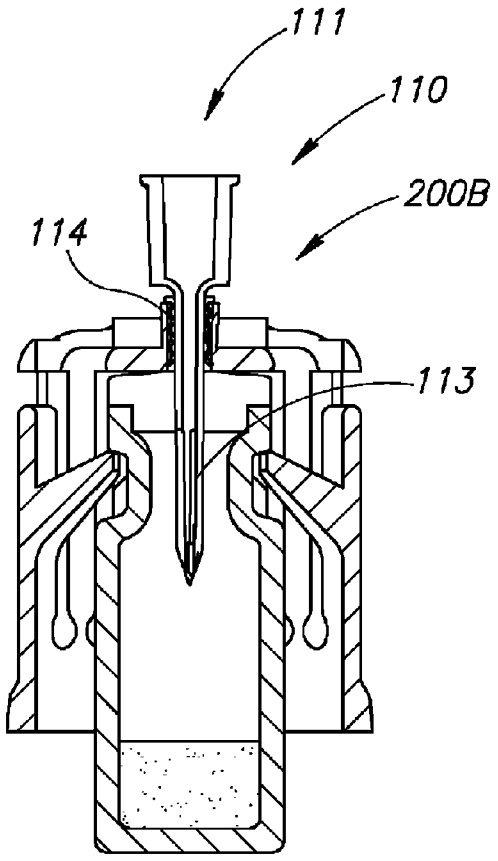
FIG. 13 is a longitudinal cross section of FIG. 12's liquid drug transfer device in a flow communication position.

FIGS. 12 and 13 show a liquid drug transfer device 110 including a universal drug vial adapter 200B and intended for use with a discrete dual ended liquid transfer member 111 formed with a female Luer connector 112 and a puncturing cannula 113 in flow communication therewith. The liquid drug transfer device 110 is similar in construction to the liquid drug transfer device 100 and differs therefrom insofar as its universal drug vial adapter 200B has a top wall 204 formed with the annular centerpiece 206 and a retainer arrangement 226 for retaining the liquid transfer member 111 above the annular centerpiece 206 ready for actuation. The puncturing cannula 113 is covered by a sheath 114 which maintains sterile conditions during storage and for use as a sealing member for use with a drug vial 20. The liquid drug transfer device 110 can be telescopically mounted on a drug vial 20 ready for subsequent actuation by downward depression of the liquid transfer member 111.

Figure 14:
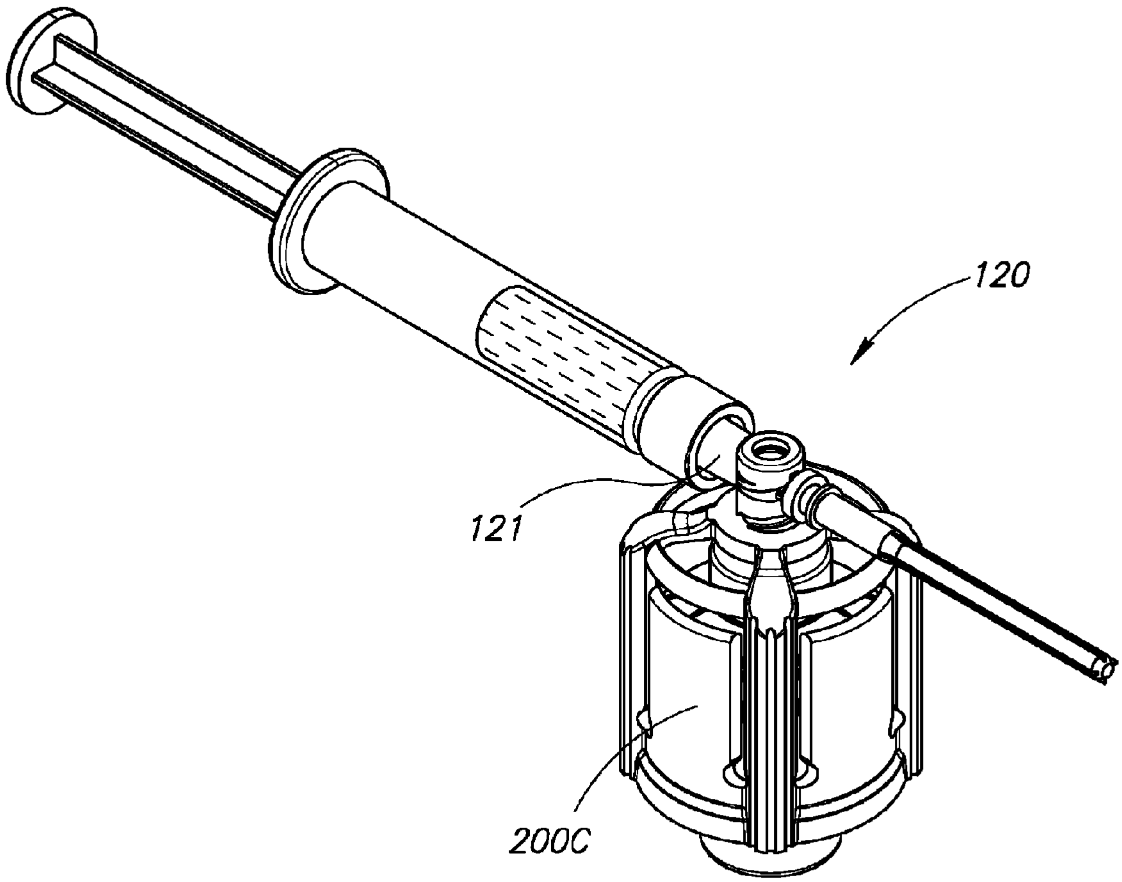
FIG. 14 is a pictorial view of a third preferred embodiment of a liquid drug transfer device in accordance with the present invention.

FIG. 14 shows a liquid drug transfer device 120 as disclosed in commonly owned U.S. Pat. No. 6,238,372 to Zinger et al. including a fluid control device 121 and a universal drug vial adapter 200C for screw thread engagement thereon.

Figure 15:
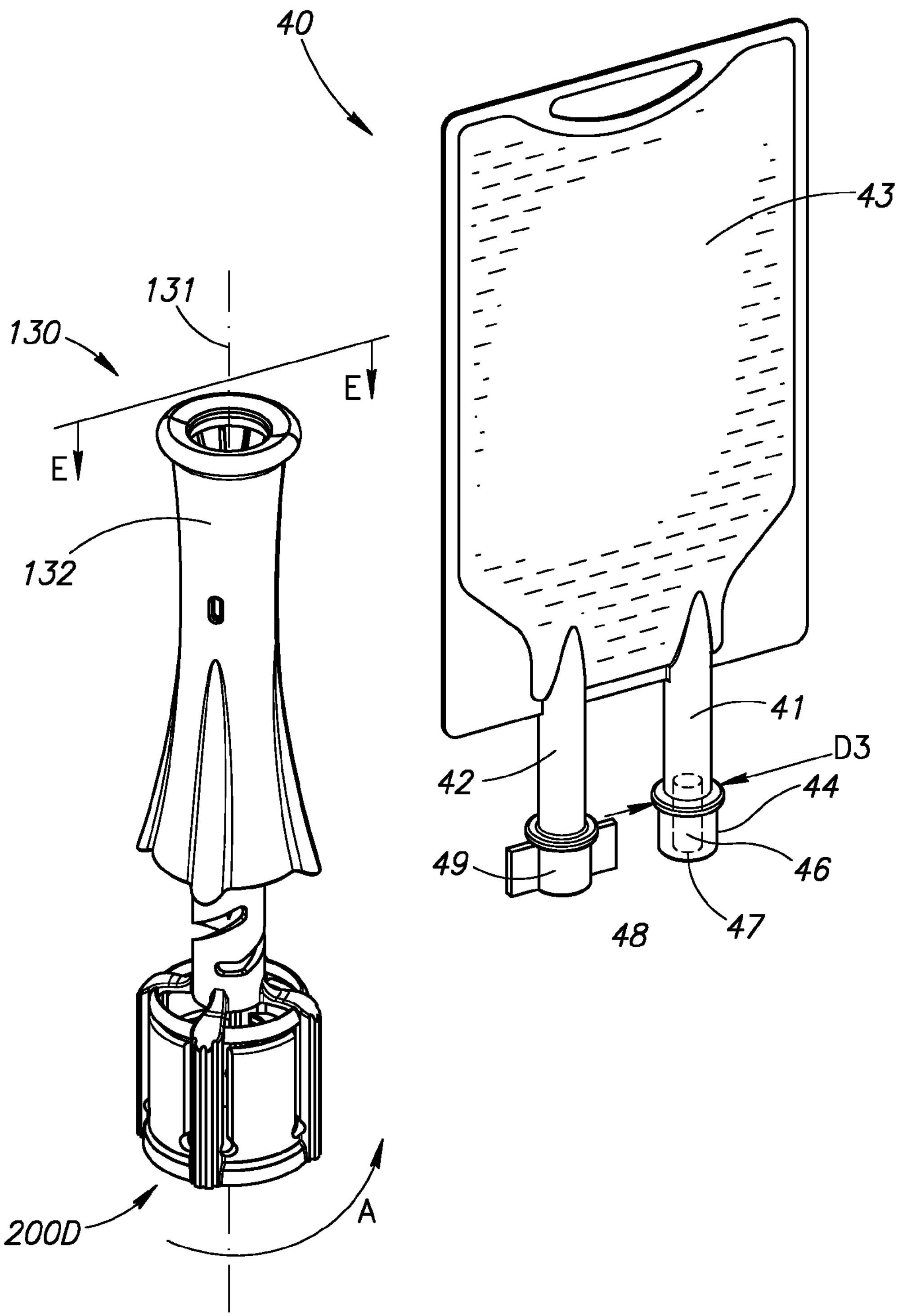
FIG. 15 is a pictorial view of a fourth preferred embodiment of a liquid drug transfer device in accordance with the present invention and an infusion liquid container.
Figure 16:
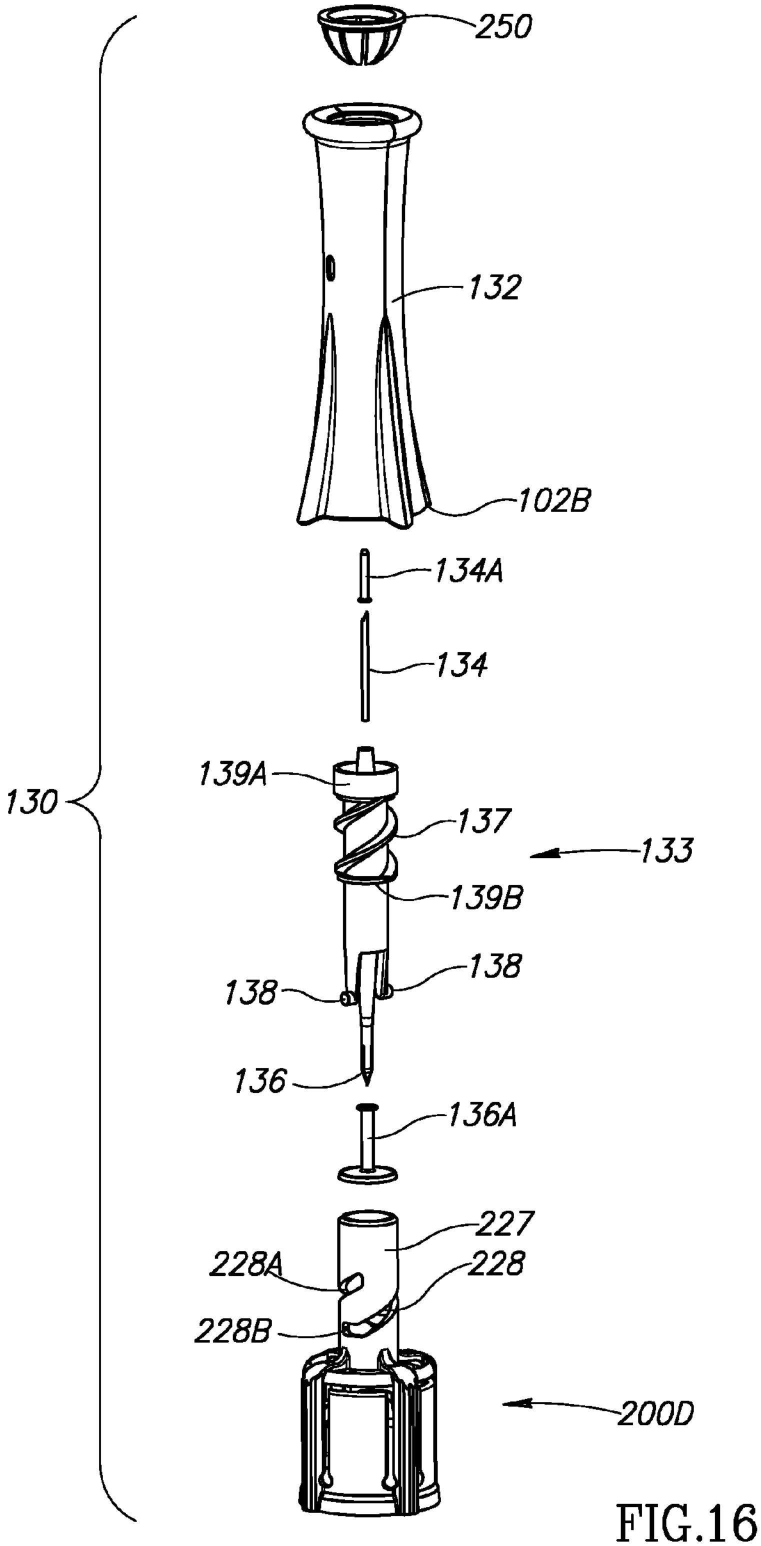
FIG. 16 is an exploded view of FIG. 15's liquid drug transfer device.

FIGS. 15 to 17 show a liquid drug transfer device 130 for use with an infusion liquid container 40 exemplary shown as an IV bag. The IV bag 40 includes an injection port 41, an administration port 42 and liquid contents 43. The IV bag ports 41 and 42 are in the form of plastic tubing. The injection port 41 terminates in an injection port tip 44 containing a self-sealing plug 46 with an exposed plug surface 47 intended for needle injection of syringe contents into the IV bag 40. The injection port tip 44 has a trailing injection port tip rim 48. The administration port 42 is typically sealed by a twist off cap 49 for insertion of an IV spike for administration purposes.

The liquid drug transfer device 130 has a longitudinal liquid drug transfer device axis 131 and includes an injection port adapter 132, a dual ended liquid transfer member 133 and a universal drug vial adapter 200D. The injection port adapter 132 is preferably provided with a universal injection port connector 250 for attachment on the injection port 41. The liquid transfer member 133 is provided with a needle 134 for puncturing the injection port 41 and terminates in a puncturing tip 136 for puncturing a drug vial stopper 31. The needle 134 is protected by a sheath 134A and the puncturing tip 136 is protected by a sheath 136A.

The liquid transfer member 133 is formed with a leading drill like bit 137 and a trailing pair of outward directed pins 138. The universal drug vial adapter 200D differs from the universal drug vial adapter 200A insofar that it has a top wall 204 formed with an axial directed tubular stem 227 on the annular centerpiece 206. The stem 227 has a pair of opposite generally helical tracks 228 for corresponding engagement by the pair of outward radial pins 138. The tracks 228 each have a start track end 228A remote from the top wall 204 and a final track end 228B adjacent the top wall 204.

The drill like bit 137 has a leading stopper 139A and a trailing stopper 139B. The injection port adapter 132 has an internal surface 141 formed with an inward radial directed leading flange 142A and an inward directed trailing flange 142B.

Figures 17A, 17B, 17C:
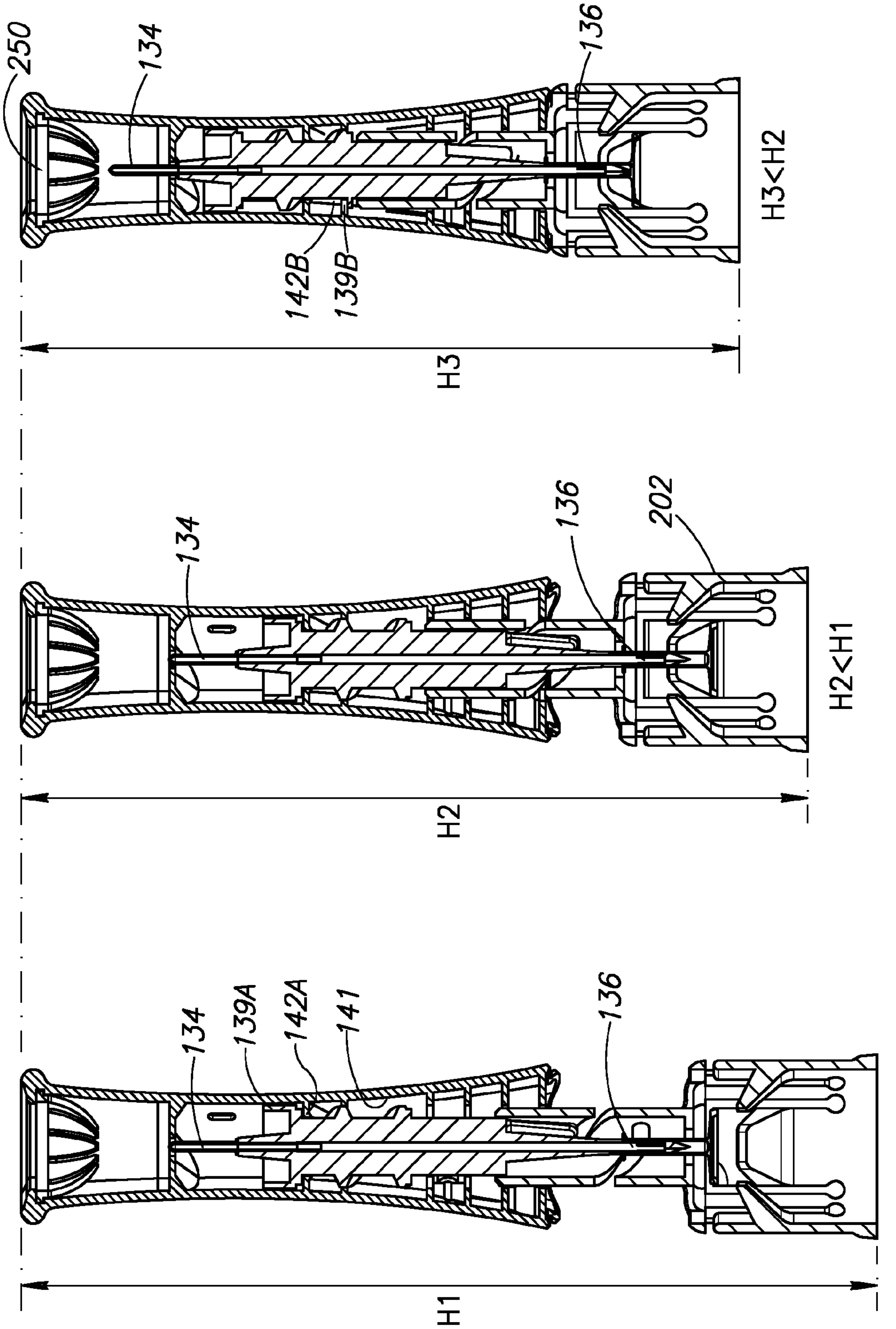
FIG. 17A is a longitudinal cross section of FIG. 15's liquid drug transfer device in an initial pre-actuated position along line E-E in FIG. 15.
FIG. 17B is a longitudinal cross section of FIG. 15's liquid drug transfer device in an intermediate position for puncturing a drug vial along line E-E in FIG. 15.
FIG. 17C is a longitudinal cross section of FIG. 15's liquid drug transfer device in an actuated position for puncturing an infusion liquid container along line E-E in FIG. 15.
Figure 18A:
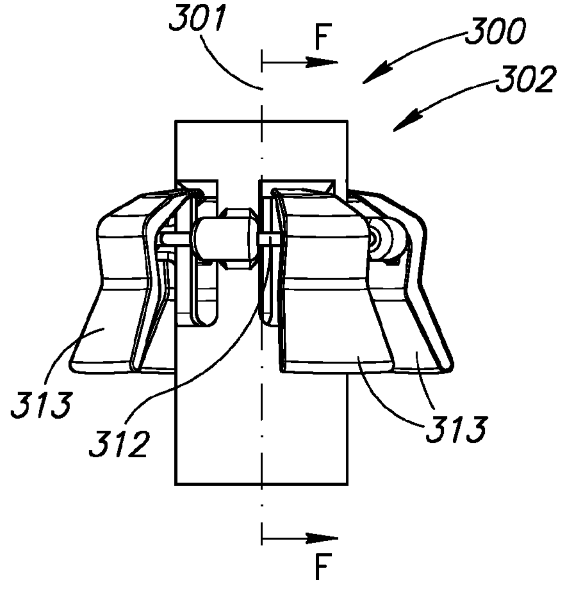
FIG. 18A is a front elevation view of a drug vial release tool in its set-up position.
Figure 18B:
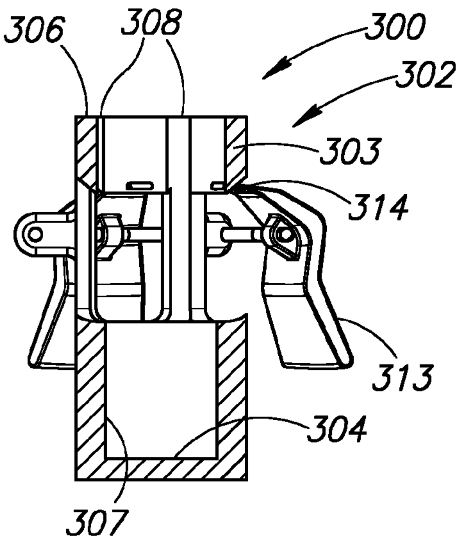
FIG. 18B is a longitudinal cross section of FIG. 18A's drug vial release tool along line F-F thereon.
Figure 19A:
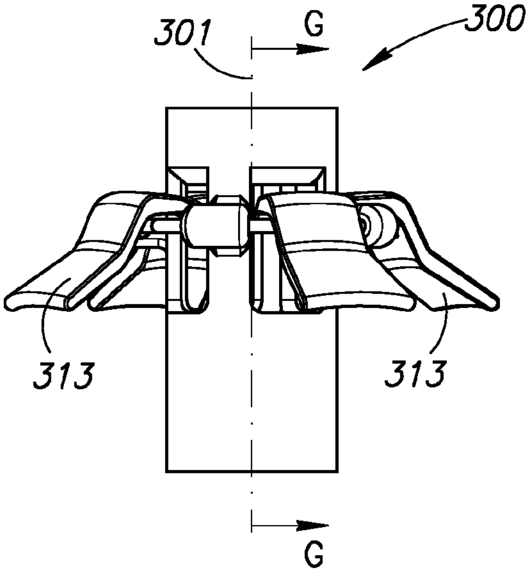
FIG. 19A is a front elevation view of the drug vial release tool in its operative vial release position to release a drug vial.
Figure 19B:
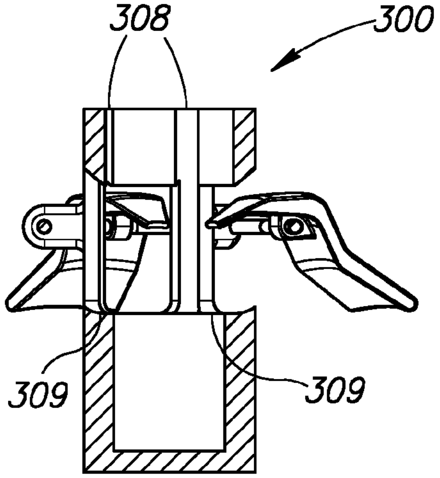
FIG. 19B is a longitudinal cross section of FIG. 19A's drug vial release tool along line G-G thereon.
Figure 20B:
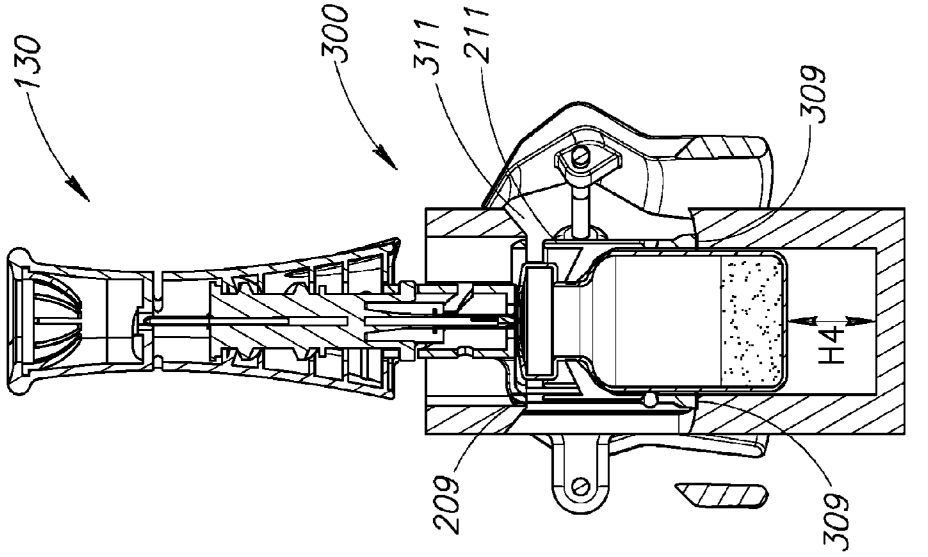
FIG. 20B is a longitudinal cross section of FIG. 20A's assemblage along line H-H thereon.
Figure 20A:
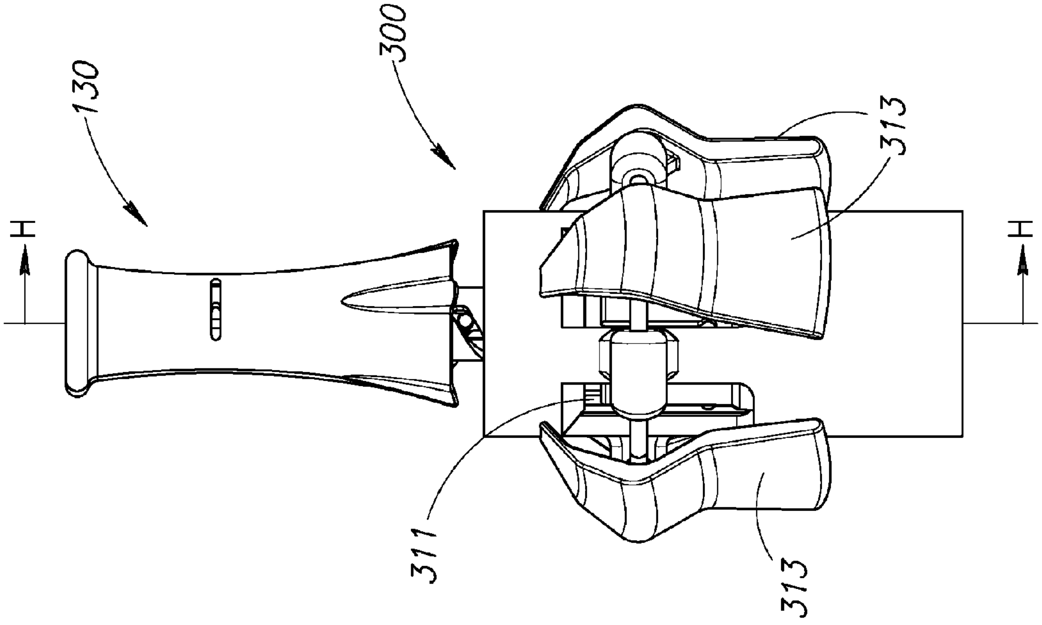
FIG. 20A is a front elevation view of the drug vial release tool in its set-up position mounted on FIG. 15's liquid drug transfer device with a pre-attached intact drug vial.
Figure 21B:
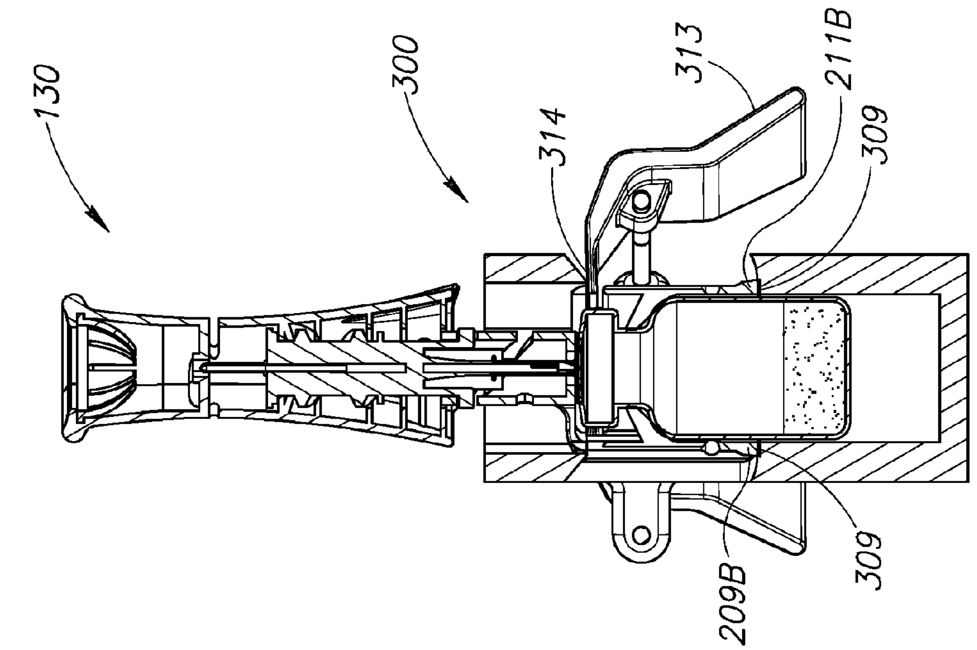
FIG. 21B is a longitudinal cross section of FIG. 21A's assemblage along line I-I thereon.
Figure 21A:
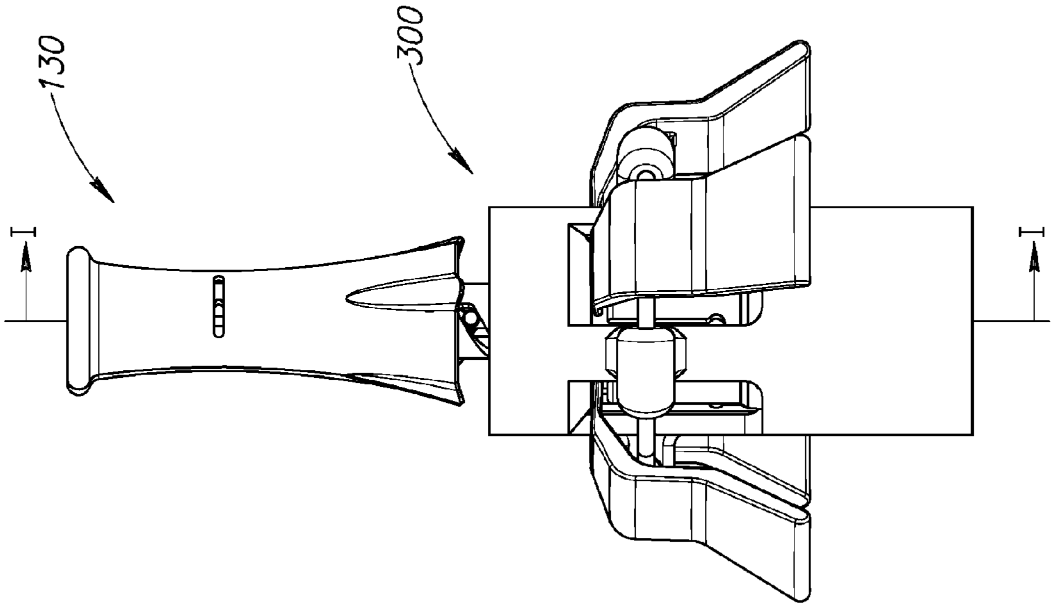
FIG. 21A is a front elevation view of the drug vial release tool in its operative vial release position mounted on FIG. 15's liquid drug transfer device with a pre-attached intact drug vial.
Figure 22B:
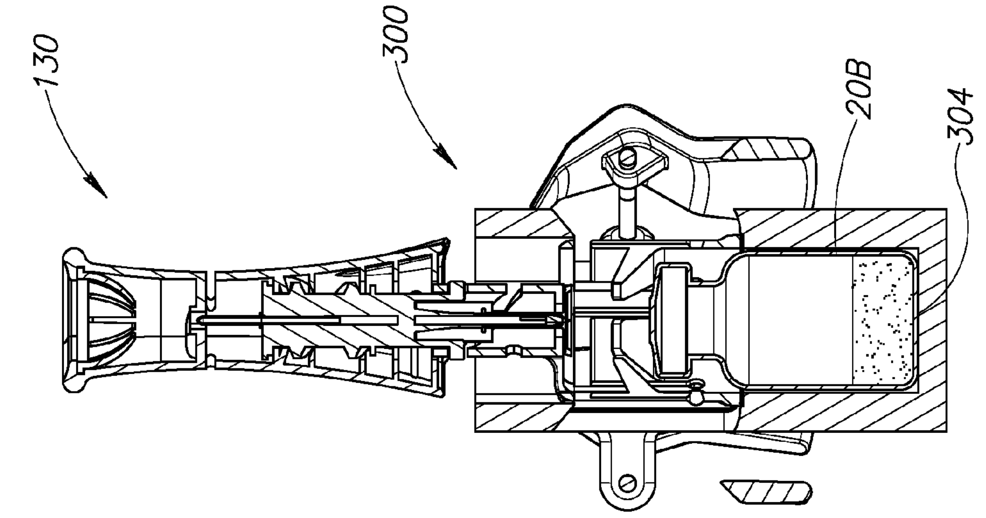
FIG. 22B is a longitudinal cross section of FIG. 22A's assemblage along line J-J thereon.
Figure 22A:
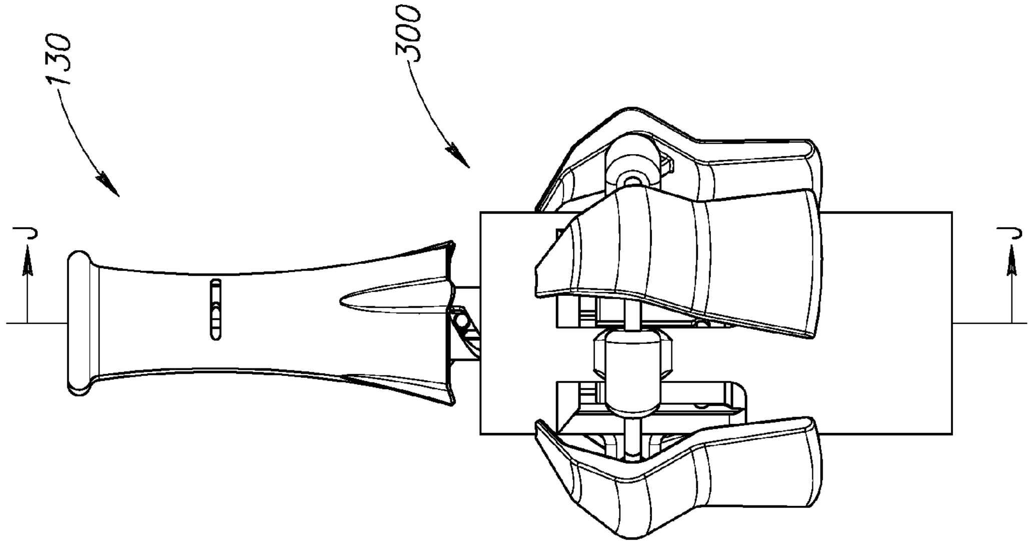
FIG. 22A is a front elevation view of the drug vial release tool mounted on FIG. 15's liquid drug transfer device and a detached intact drug vial.

FIG. 17A shows the leading stopper 139A is disposed on the leading flange 142A in an initial pre-actuated position of the liquid drug transfer device 130. The puncturing tip 136 is deployed above or at the top wall 204 such that an intact drug vial 20 can be telescopically clamped in the universal drug vial adapter 200D for subsequent use. On telescopic mounting a drug vial in the universal drug vial adapter 200D, the puncturing tip 136 is spaced apart from its uppermost drug vial surface 32. The liquid drug transfer device 130 has a height H1 in its initial pre-actuated position.

FIG. 17B shows initial manual actuation rotation of the universal drug vial adapter 200D in a clockwise tightening direction around the longitudinal axis 131 as depicted by arrow A in FIG. 15 leads to the universal drug vial adapter 200D traveling along the liquid transfer member 133 until the outward directed pins 138 stop at the final track ends 228B. This linear movement causes the puncturing tip 136 to puncture through a drug vial stopper 31 into a drug vial interior 28 of a previously clamped drug vial 20 for establishing flow communication with its drug vial interior 28. The liquid drug transfer device 130 has a height H2 in its intermediate drug vial puncturing position where H2<H1.

FIG. 17C shows continuing manual actuation rotation of the universal drug vial adapter 200D in the same clockwise tightening direction leads to the combined movement of the liquid transfer member 133 and the universal drug vial adapter 200D until the trailing stop 141B stops against the trailing flange 142. This linear movement urges the needle 134 towards the universal injection port connector 250 for puncturing an injection port 41, thereby establishing flow communication between an infusion liquid container 40 and a drug vial 20. The liquid drug transfer device 130 has a height H3 in its actuated infusion liquid container puncturing position where H3<H2.

The liquid drug transfer device 130 is preferably provided with a pre-attached intact drug vial 20. The liquid drug transfer device 130 can optionally be pre-attached to an infusion liquid container 40. Accordingly, a user is required to execute a single manual actuation rotation for establishing flow communication between an infusion liquid container and a drug vial.

FIGS. 18 to 23 show a drug vial release tool 300 for releasing an intact drug vial 20 from the liquid drug transfer device 130 in its initial set-up state before having undergone a manual actuation rotation. The construction and operation of the drug vial release tool 300 is shown with reference to a drug vial 20B and equally applies to a drug vial 20A.

The drug vial release tool 300 has a longitudinal tool axis 301 and includes an open-topped housing 302 having a peripheral wall 303, a bottom wall 304 and a top rim 306. The housing 302 is intended to slidingly receive the universal drug vial adapter 200D with a pre-attached intact drug vial 20. The peripheral wall 303 has an internal surface 307 having with four longitudinal directed slots 308 for slidingly receiving the four equispaced downward depending flex member supports 209, 211, 212 and 213 for ensuring correct rotational alignment of the universal drug vial adapter 200D in the drug vial release tool 300. The longitudinal directed slots 308 are each formed with a stopper 309 for stopping the sliding insertion of the universal drug vial adapter 200D into the drug vial release tool 300 such that an intact drug vial 20 is at a height H4 above the inside bottom wall 304 (see FIG. 20B). In the case of manual actuation rotation of the liquid drug transfer device 130, the universal drug vial adapter 132 prevents full insertion of the universal liquid drug adapter 200D into the drug vial release tool 300 as shown in FIGS. 23A and 23B in which the punctured drug vial is at a height H5 above the bottom wall 304.

The housing 302 is formed with four longitudinal directed rectangular apertures 311 in registration with the four resiliently flexible upward depending flex members 221, 222, 223 and 224 on sliding insertion of the universal drug vial adapter 200D thereinto. The drug vial release tool 300 includes an annular railing 312 encircling the housing 302. The railing 312 supports four pivotal release members 313 each having a release member rim 314. The release members 313 have a set-up position enabling free sliding insertion of the universal drug vial adapter 200D into the housing 302 (see FIGS. 20A and 20B). The release members 313 are operable to an operative position such that their release member rims 314 are disposed in the separations between the top wall 204 and the flexible flex members 221, 222, 223 and 224 (see FIGS. 21A and 21B). The release members 313 are manually operated to outwardly flex the flex members 221, 222, 223 and 234 with respect to the longitudinal tool axis 301 thereby freeing the drug vial 20 which drops onto the bottom wall 304 (see FIGS. 22A and 22B).

Figure 23A:
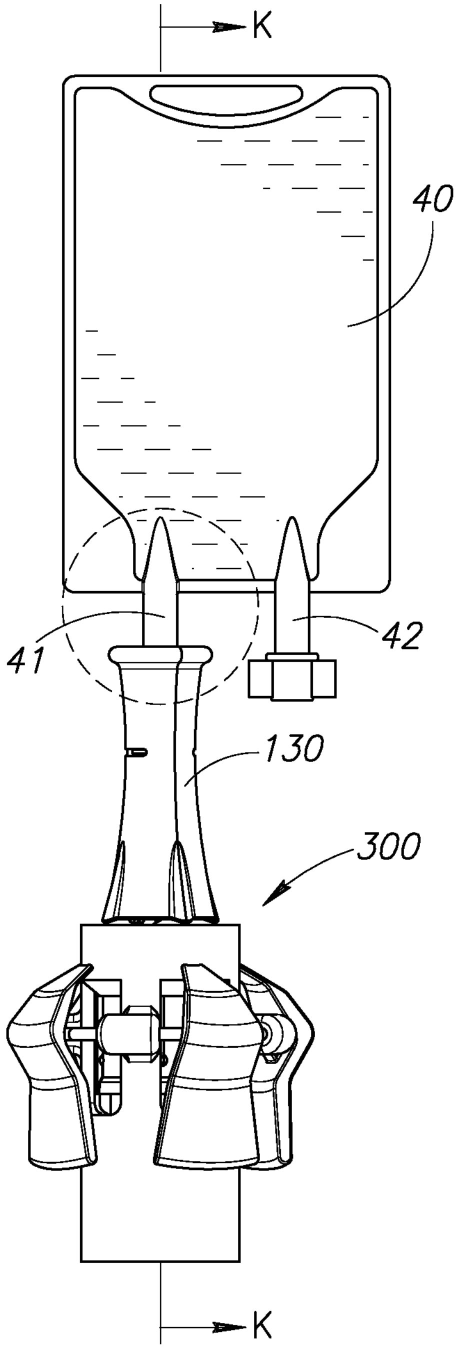
FIG. 23A is a front elevation view of the drug vial release tool in an inoperative position mounted on FIG. 15's liquid drug transfer device with a punctured drug vial after a partial manual actuation rotation.
Figure 23B:
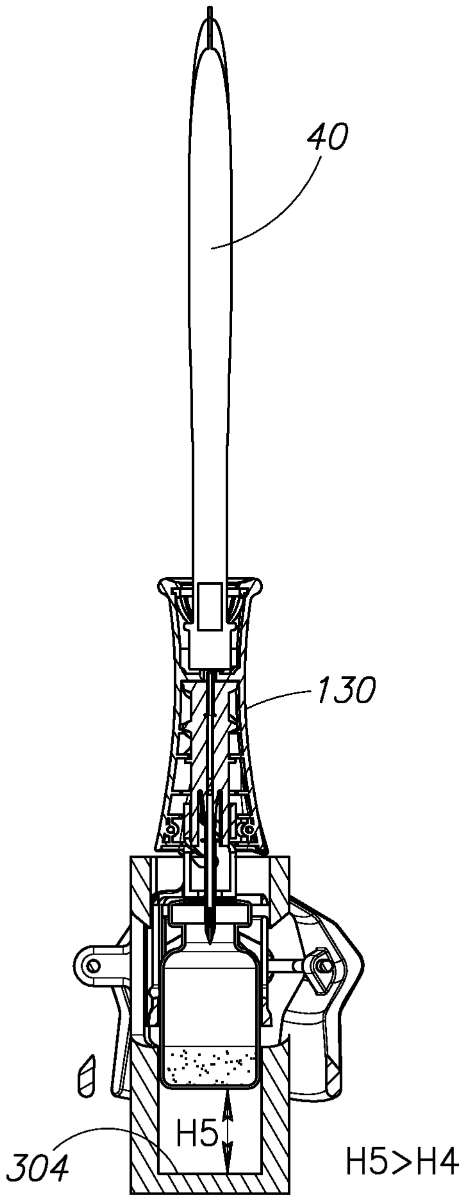
FIG. 23B is a longitudinal cross section of FIG. 23A's assemblage along line K-K thereon.
Figure 24:
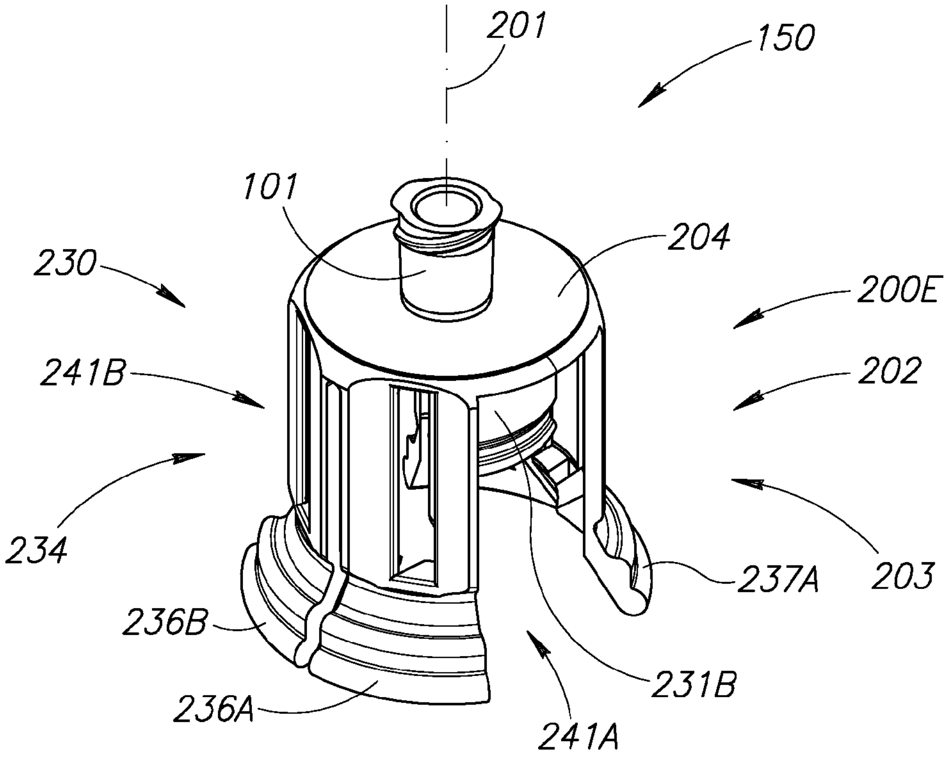
FIG. 24 is a front top perspective view of a fifth preferred embodiment of a liquid drug transfer device in accordance with the present invention.
Figure 25:
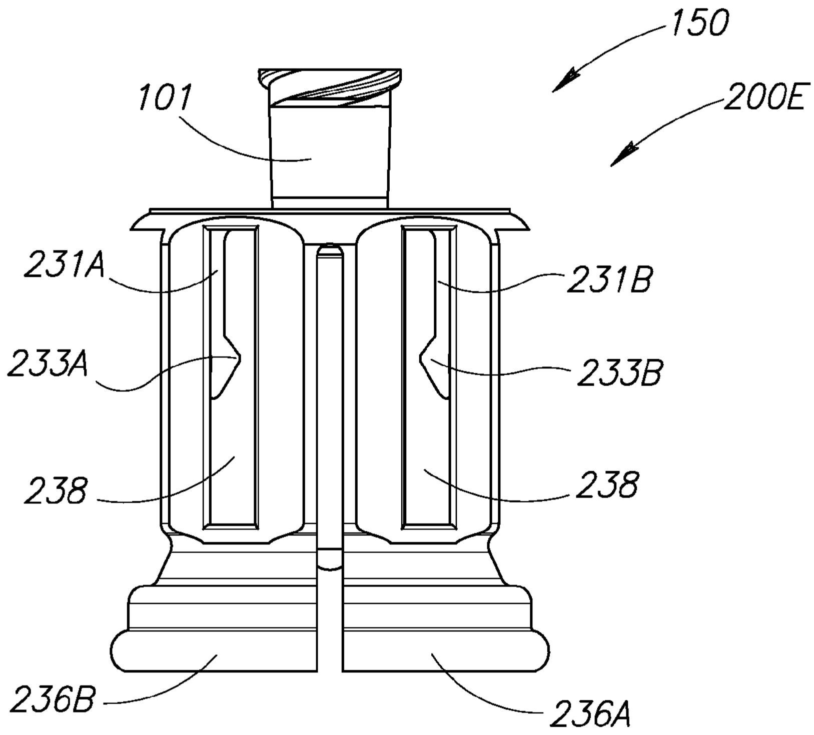
FIG. 25 is a front elevation view of FIG. 24's liquid drug transfer device.
Figure 26:
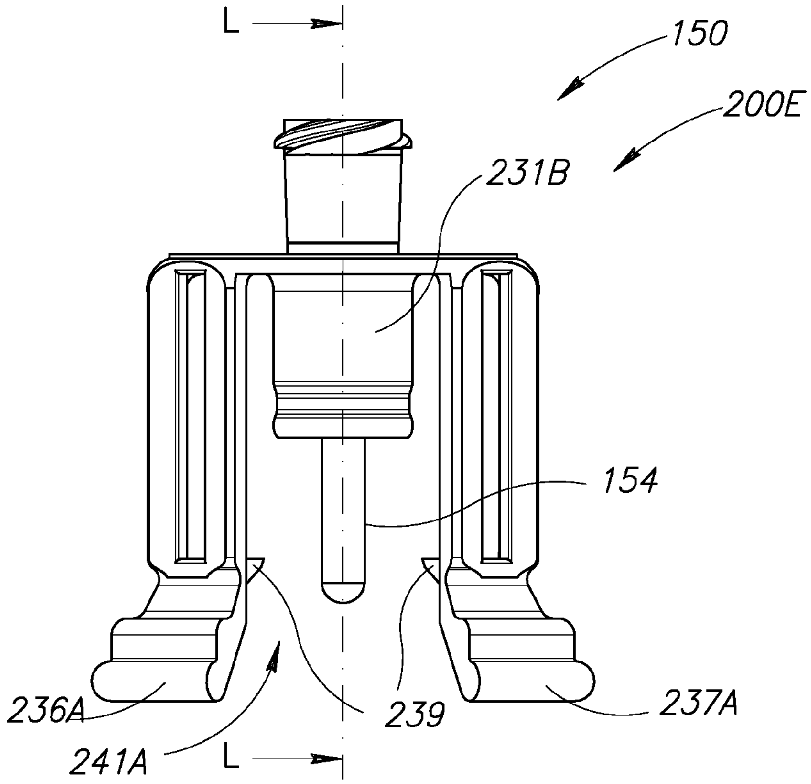
FIG. 26 is a right side elevation view of FIG. 24's liquid drug transfer device.
Figure 27:
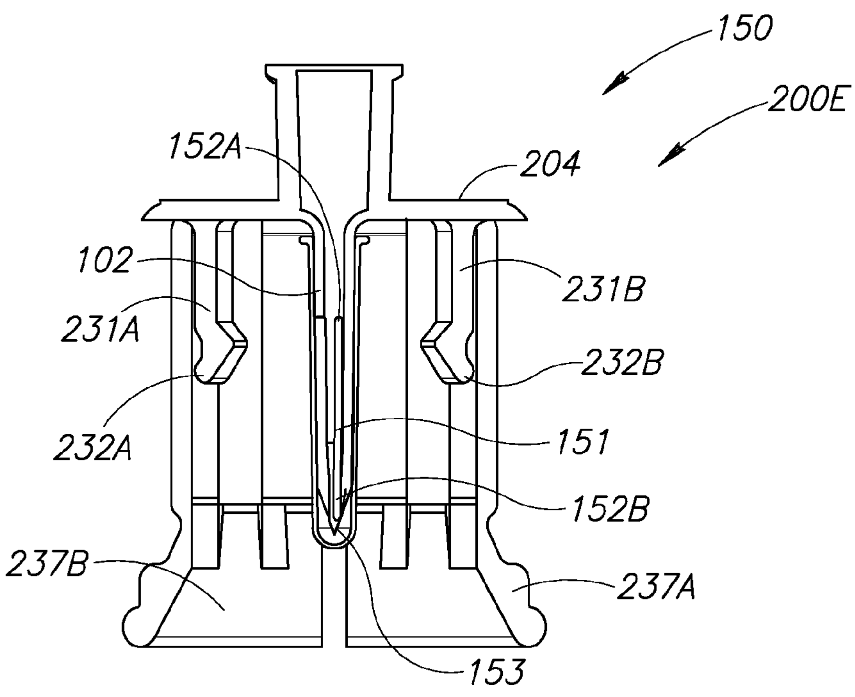
FIG. 27 is a longitudinal cross section of FIG. 24's liquid drug transfer device along line L-L on FIG. 26.

FIGS. 23A and 23B show that in the case the liquid drug transfer device 130 has been partially actuated to puncture the drug vial 20, the universal drug vial adapter 200D rests on the top rim 306 on its insertion into the drug vial release tool 300, the release members 313 are not aligned with the separations between the top wall 204 and the flex members 221, 222, 223 and 224 but rather their release member tips 314 directly face the flex members 221, 222, 223 and 224 and are therefore inoperable to release the punctured drug vial 20.

FIGS. 24 to 33 show a liquid drug transfer device 150 for use with a syringe 10, and a drug vial of a small drug vial 20A and a large drug vial 20B. The liquid drug transfer device 150 is similar to the liquid drug transfer device 100 insofar it includes a universal drug vial adapter 200E, a female Luer connector 101, and a tubular puncturing member 102 in flow communication with the female Luer connector 101 for enabling flow access to a drug vial interior 28. The universal drug vial adapter 200E is similar to the universal drug vial adapter 200A insofar it has a longitudinal drug vial adapter axis 201, a skirt 202, a drug vial cavity 203 for snugly telescopically receiving at least a top part of a drug vial 20B therein and therefore inherently a top part of a drug vial 20A, and a top wall 204 transverse to the longitudinal drug vial adapter axis 201.

The puncturing member 102 has a pair of elongated flow apertures 151 each having a proximal end 152A adjacent the top wall 204 and a distal end 152B adjacent a puncturing tip 153. The proximal ends 152A are adjacent the top wall 204 to ensure that the entire liquid contents of a drug vial 20A can be aspirated therefrom on inversion of an assemblage of the liquid drug transfer device 150 and a drug vial 20A. The distal ends 152B are adjacent the puncturing tip 153 to ensure that the puncturing member 102 is in flow communication with a drug vial 20B's drug vial interior 28 in an assemblage of the liquid drug transfer device 150 and a drug vial 20B.

Figure 29:
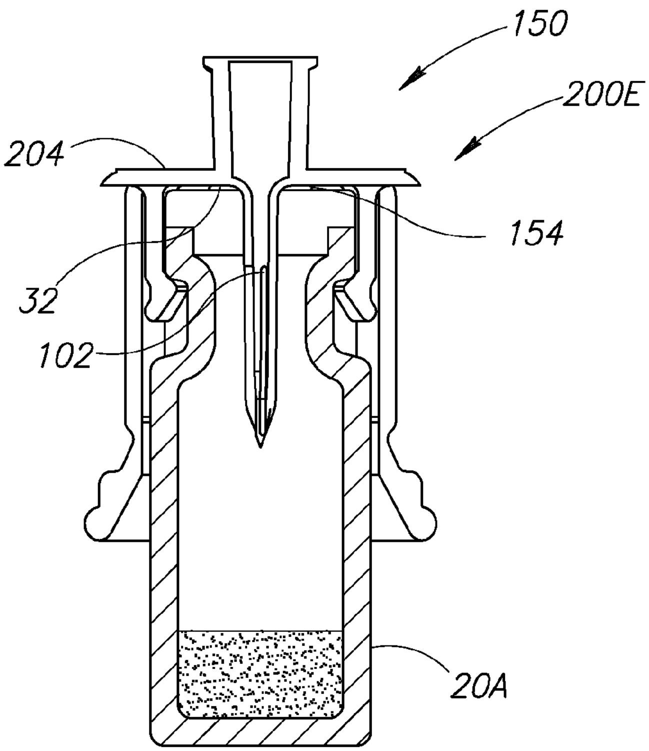
FIG. 29 is a longitudinal cross section of FIG. 28's assemblage along line M-M thereon.
Figure 31:
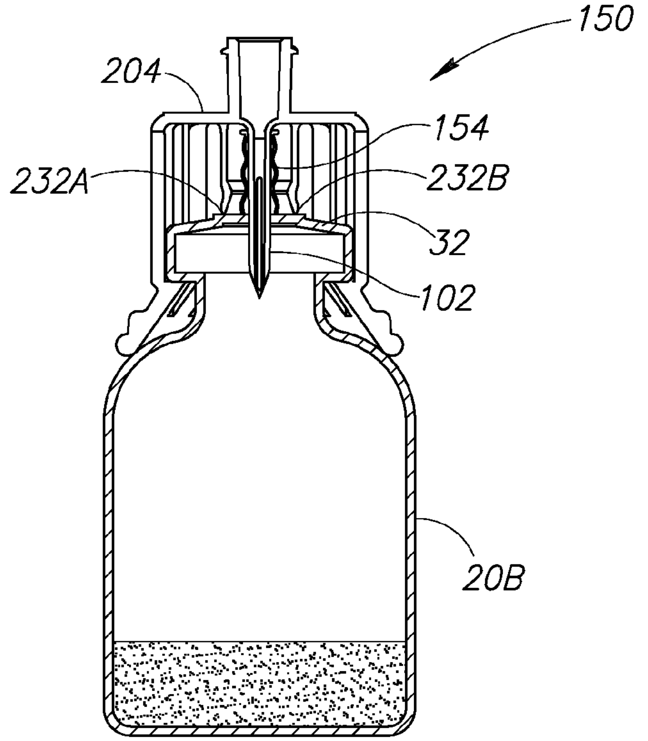
FIG. 31 is a longitudinal cross section of FIG. 30's assemblage along line N-N thereon.

The liquid drug transfer device 150 includes a thin sheath 154 covering the puncturing member 102. The sheath 154 is urged towards the top wall 204 on mounting the liquid drug transfer device 150 on a drug vial 20A and a drug vial 20B. In the former case, FIG. 29 shows the sheath 154 is flattened between the top wall 204 and the drug vial 20A's uppermost drug vial surface 32. In the latter case, FIG. 31 shows the sheath 154 takes on a bellows like appearance between the top wall 204 and the drug vial 20B's uppermost drug vial surface 32. The sheath 154 acts as a sealing member for sealing the proximal ends 152A of the elongated flow apertures 151 which are exposed between the top wall 204 and the drug vial 20B's uppermost drug vial surface 32.

The skirt 202 includes a set of minor flex members 230 for telescopically clamping on a drug vial 20A's drug vial head. The set of minor flex members 230 includes a pair of opposite minor flex members 231A and 231B for telescopically clamping on a drug vial 20A's drug vial head 24. The minor flex members 231 each have a free minor flex member end 232A and 232B distal from the top wall 204 and an inner directed rim 233A and 233B for snap fitting on a drug vial 20A's drug vial head 24.

The skirt 202 includes a set of major flex members 234 for telescopically clamping on a drug vial 20B's drug vial closure 33. The set of major flex members 234 includes a first pair of adjacent major flex members 236A and 236B and a second pair of adjacent major flex members 237A and 237B opposite the first pair of adjacent major flex members 236A and 236B. The set of major flex members 234 includes pairs of adjacent major flex members 236 and 237 for ensuring they clamp two opposite major lengths of the periphery of a drug vial 20B's drug vial closure 33.

The major flex members 236 and 237 are each formed with a longitudinal directed window 238 and an inner directed rim 239 for snap fitting on a drug vial 20B's drug vial closure 33. The major flex members 236A and 237A are spaced apart to leave a separation 241A therebetween. The major flex members 236B and 237B are spaced apart to leave a separation 241B therebetween. The minor flex members 231 are aligned with the separations 241 whereby, on telescopically clamping the liquid drug transfer device 150 on a drug vial 20A, the minor flex members 231 are unhindered by the major flex members 236 and 237 to outwardly flex relative to the longitudinal drug vial adapter axis 201.

Figure 28:
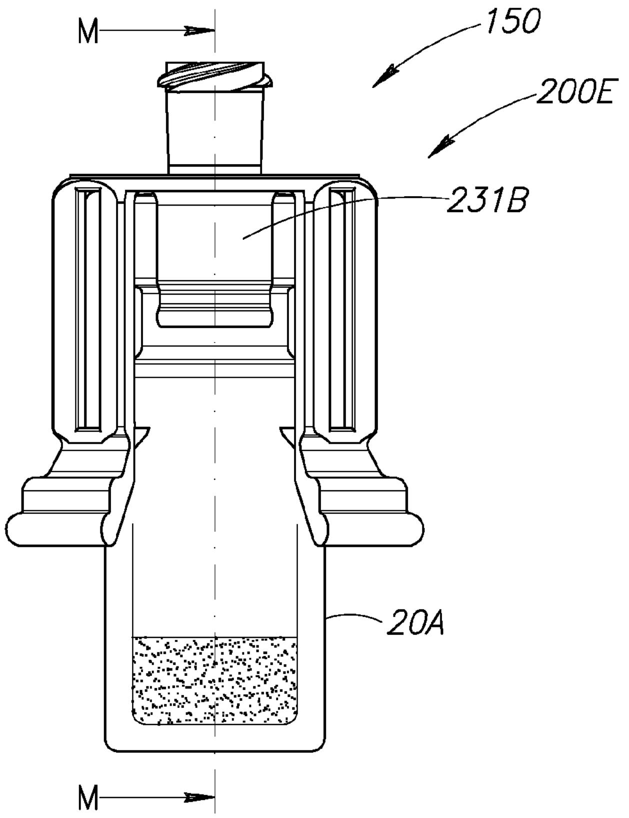
FIG. 28 is a right side elevation view of FIG. 24's liquid drug transfer device telescopically clamped on a small drug vial.

FIGS. 28 and 29 show the liquid drug transfer device 150 mounted on a drug vial 20A. The puncturing member 102 entirely punctures through its drug vial stopper 31 such that the proximal ends 152A are within its drug vial interior 28.

Figure 30:
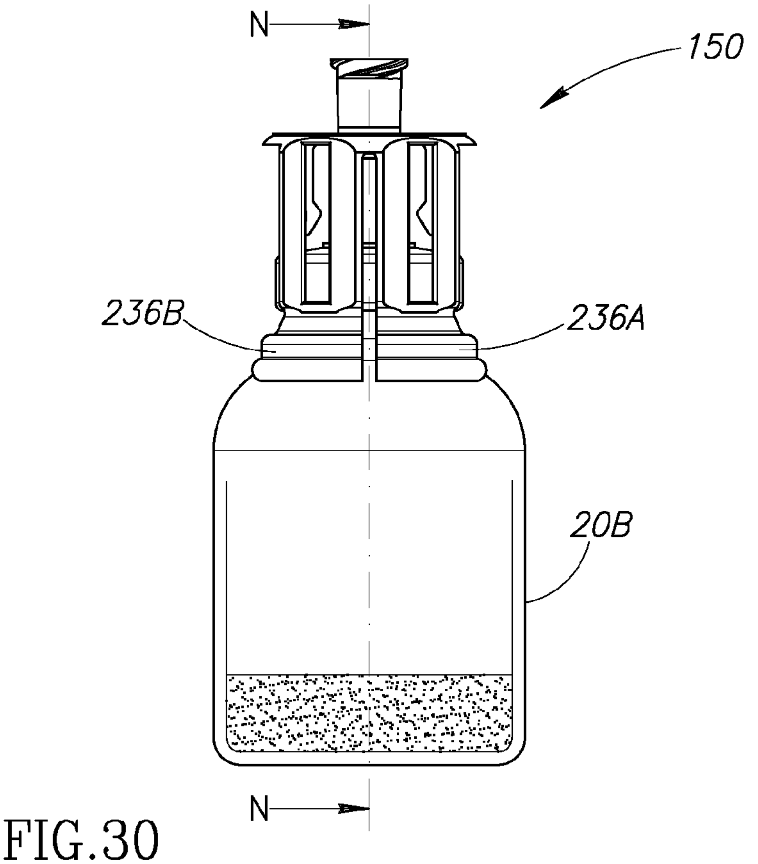
FIG. 30 is a front elevation view of FIG. 24's liquid drug transfer device mounted on a large drug vial.

FIGS. 30 and 31 show the liquid drug transfer device 150 mounted on a drug vial 20B. The set of minor flex members 230 acts as an abutment member to distance the drug vial 20B from the top wall 204 whereupon the drug vial 20B's uppermost drug vial surface 32 underlies the minor flex member free ends 232A and 232B.

The top portion of puncturing member 102 remains exposed between the top wall 204 and the drug vial's uppermost drug vial surface 32. The sheath 154 assumes a bellows like appearance between the top wall 204 and the drug vial 20B's uppermost drug vial surface 32 for acting as a sealing member for the exposed lengths of the elongated flow apertures 151.

Figure 32:
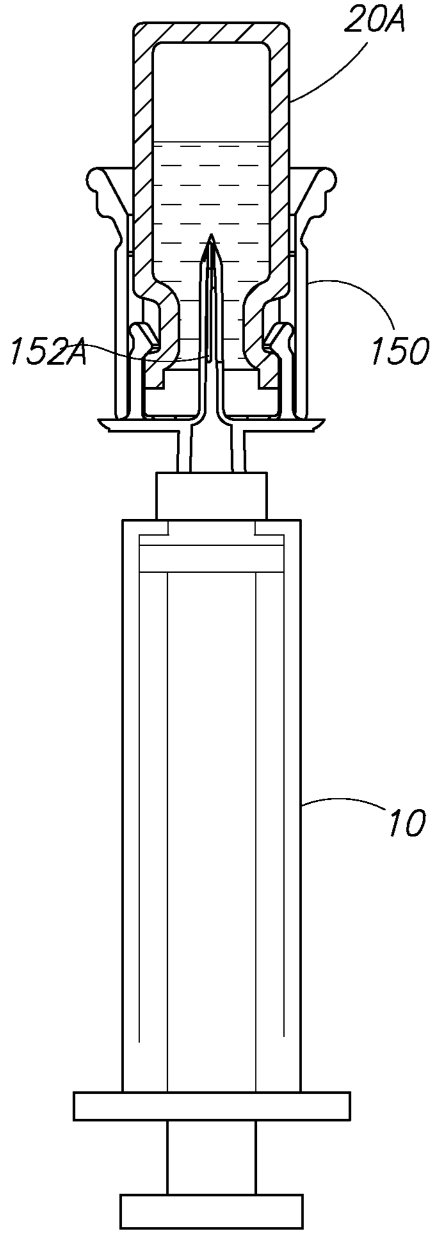
FIG. 32 is a pictorial view showing syringe aspiration of liquid contents from FIG. 28's assemblage.

FIG. 32 shows a syringe 10 attached to the liquid drug transfer device 150 mounted on a drug vial 20A for mixing, reconstitution and aspiration purposes.

Figure 33:
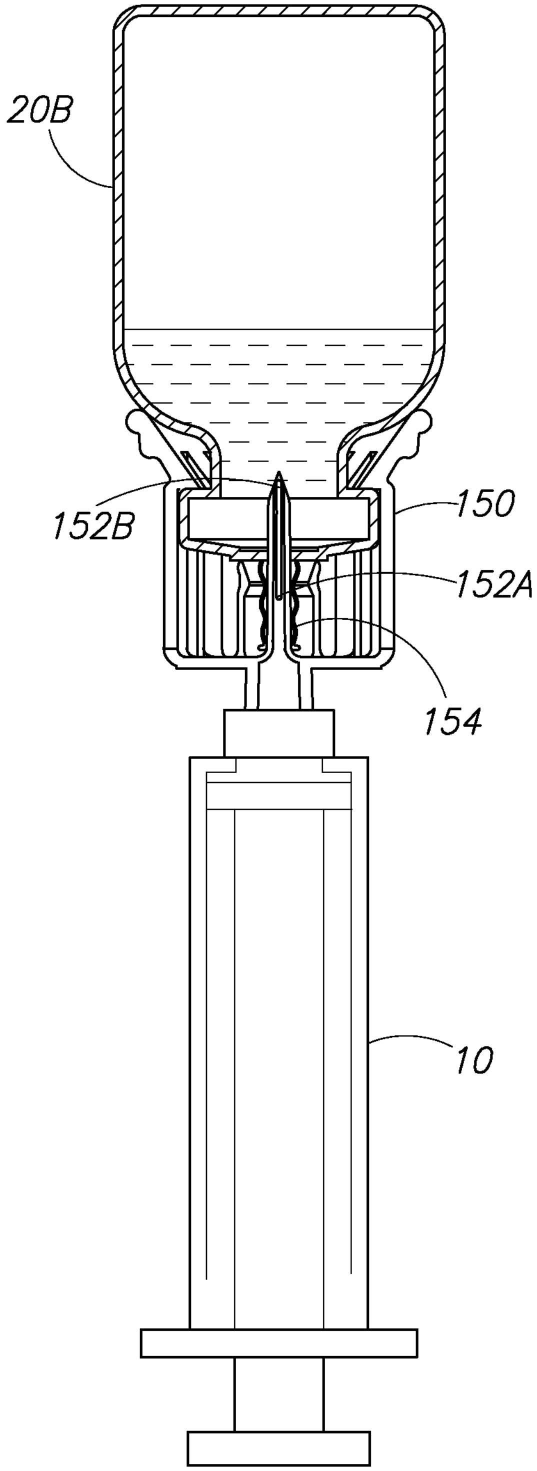
FIG. 33 is a pictorial view showing syringe aspiration of liquid contents from FIG. 30's assemblage.

FIG. 33 shows a syringe 10 attached to the liquid drug transfer device 150 mounted on a drug vial 20B for mixing, reconstitution and aspiration purposes.

Figure 34:
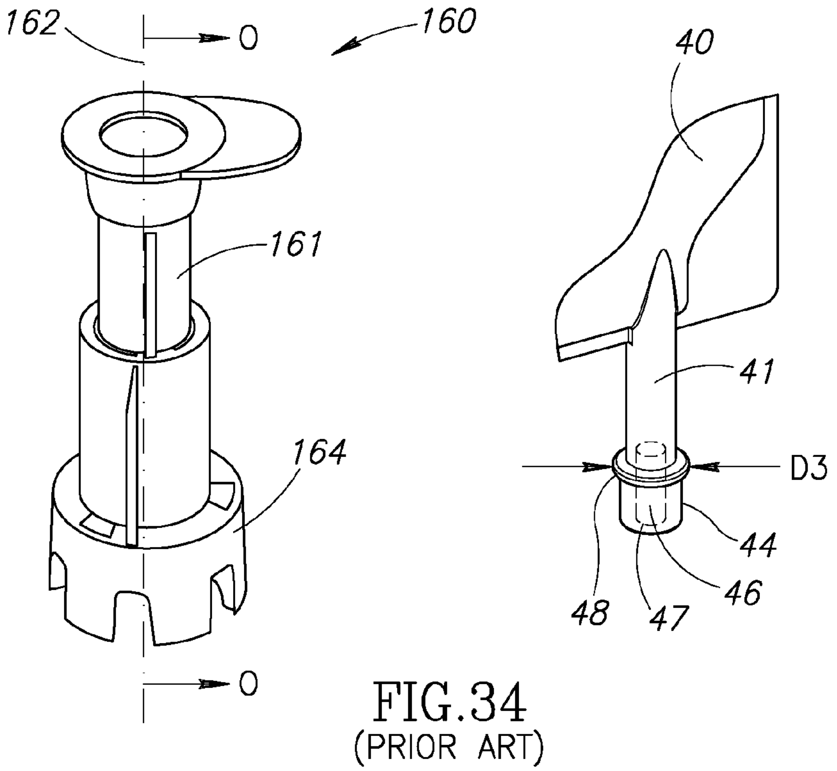
FIG.34 (PRIOR ART)
FIG. 34 is a front perspective view of a conventional liquid drug transfer device for attaching to an injection port.

FIG. 34 shows a liquid drug transfer device 160 with an injection port connector 230 for mounting on a particular sized injection port 41 having an injection port tip 44 with a self-sealing plug 46, an exposed plug surface 47 and a trailing injection port tip rim 48. The liquid drug transfer device is commercially available under the trade name VIAL-MATE Adaptor Device from Baxter Healthcare Corporation. The product sheet is available online at http://www.baxtermedicationdeliveryproducts.com/drug-delivery/vialmate.html.

The product sheet indicates that the VIAL-MATE Adaptor Device is suitable only for single dose vials with 20 mm closure and VIAFLEX containers also available from Baxter Healthcare Corporation.

Figure 35:
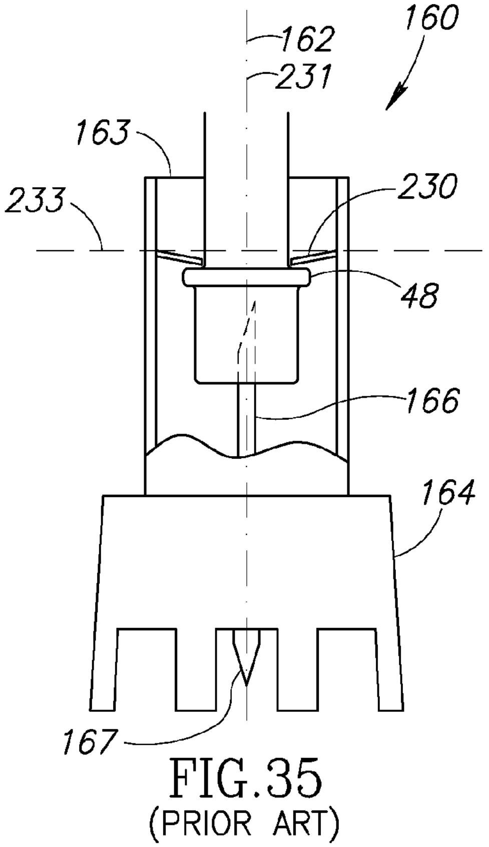
FIG.35 (PRIOR ART)
FIG. 35 is a longitudinal cross section of FIG. 34's liquid drug transfer device along line O-O thereon deployed with a conventional injection port connector for attaching to an injection port.

FIG. 35 shows the liquid drug transfer device 160 includes an open-ended housing 161 having a longitudinal housing axis 162, an access aperture 163 and a vial adapter 164. The open ended housing 161 includes a needle 166 for puncturing an injection port 41 and a puncturing member 167 downward depending into the vial adapter 164 in flow communication with the needle 166.

Figure 36:
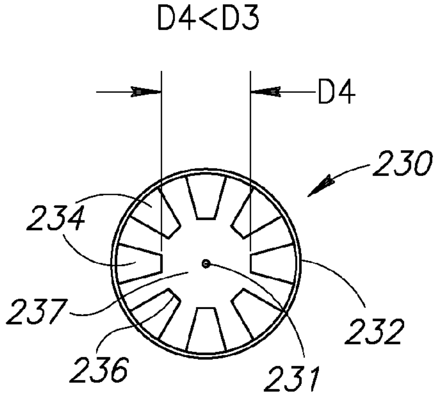
FIG.36 (PRIOR ART)
FIG. 36 is a top view of FIG. 35's conventional injection port connector.

FIG. 36 shows a conventional injector port connector 230 deployed in the open ended housing 161 towards the access aperture 163. The injector port connector 230 includes a longitudinal connector axis 231 in co-axial alignment with the longitudinal housing axis 162. The injection port connector 230 includes a circular support ring 232 defining a horizontal plane 233 transverse to the longitudinal housing axis 162. The support ring 232 includes a multitude of straight connector members 234 each terminating in a free connector member end 236 disposed toward the longitudinal housing axis 162. The free connector member ends 236 converge to define a generally circular connector aperture 237 underlying the horizontal plane 233. The connector aperture 237 has a connector aperture diameter D4 where D4<D3.

The liquid drug transfer device 160 is designed for a particular sized injection port 41 to be forcibly slidingly inserted through the connector aperture 237 from the direction of the access aperture 163 towards the vial adapter 164 whereupon the free connector member ends 236 snap behind the trailing injection port tip rim 48. However, the injection port 41 is undesirably capable of being readily withdrawn from the open-ended housing 161 on application of a relatively small outward longitudinal withdrawal force in the direction of the access aperture 163.

Figure 37:
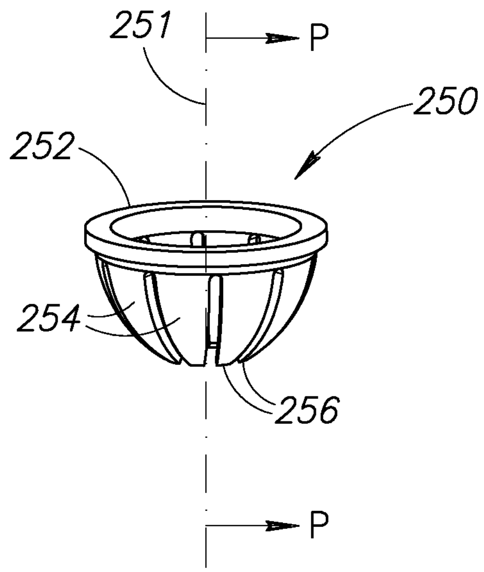
FIG. 37 is a perspective view of a universal injection port connector in accordance with the present invention.
Figure 38:
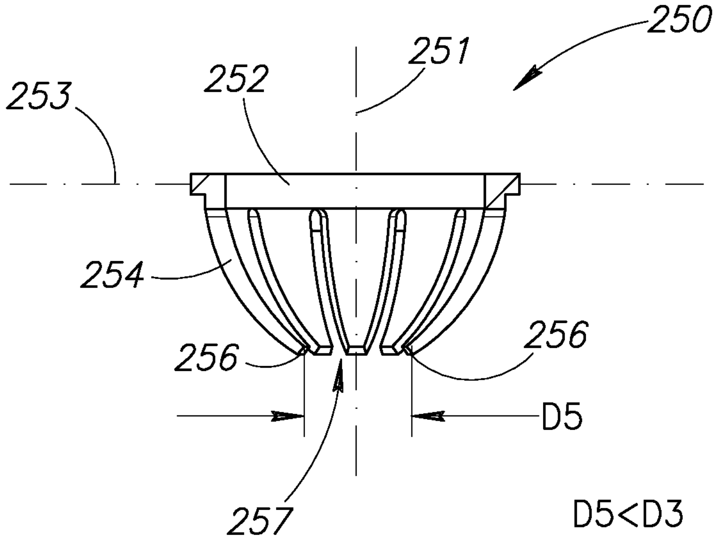
FIG. 38 is a longitudinal cross section of FIG. 37's universal injection port connector along line P-P thereon.

FIGS. 37 and 38 show a universal injection port connector 250 for mounting on different sizes of injection ports 41. The universal injection port connector 250 has the same basic construction as the injector port connector 230 as follows: The universal injection port connector 250 has a longitudinal axis 251, a closed support ring 252 defining a horizontal plane 253, a multitude of connector members 254 each resiliently flexibly mounted on the support ring 252 and terminating in a free connector member end 256 converging towards a connector aperture 257 parallel to the horizontal plane 253. The closed support ring 252 is preferably circular but can be formed in other closed shapes, for example, oval, and the like.

The universal injection port connector 250 differs from the conventional injection port connector 230 insofar as the former has curved connector members 254 as opposed to the latter's straight connector members 234 such that the universal injection port connector 250 assumes an overall bowl like shape. The connector aperture 257 has a connector aperture diameter D5 where D5<D3 such that forced sliding insertion of an injection port tip 44 through the connector aperture 257 from the direction of the support ring 252 outwardly flexes the connector members 254 from their non-flexed position relative to the longitudinal connector axis 251 for snapping behind the trailing injection port rim 48, thereby precluding sliding withdrawal of the injection port tip 44 in a reverse direction to the forced sliding insertion. By virtue of the curved shape of its connector members 254, the universal injection port connector 250 is capable of being attached on different sizes of injection ports 41. Moreover, by virtue of its curved connector members 254, the universal injection port connector 250 is more capable of withstanding an outward longitudinal withdrawal force than the conventional injection port connector 230.

Figure 39:
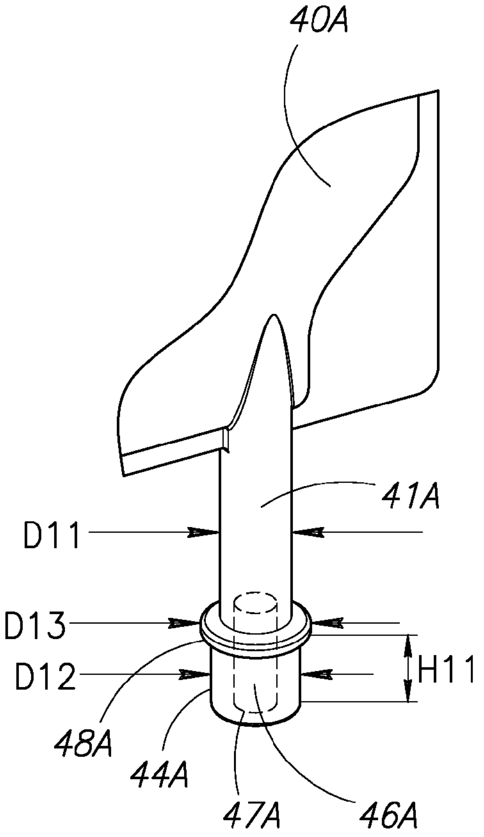
FIG. 39 is a front perspective view of an infusion bag with a so-called small injection port.

FIG. 39 shows an infusion bag 40A having a so-called small injection port 41A having an injection port tip 44A with a self-sealing plug 46A, an exposed plug surface 47A and a trailing injection port tip rim 48. The injection port 41A has an external diameter D11. The injection port tip 44A has an external tip diameter D12 and a tip height H11. The trailing injection port tip rim 48A has an external diameter D13. D11 is 6.5 mm, D12 is 7.5 mm, H11 is 7.5 mm and D13 is 10.5 mm.

Figure 40:
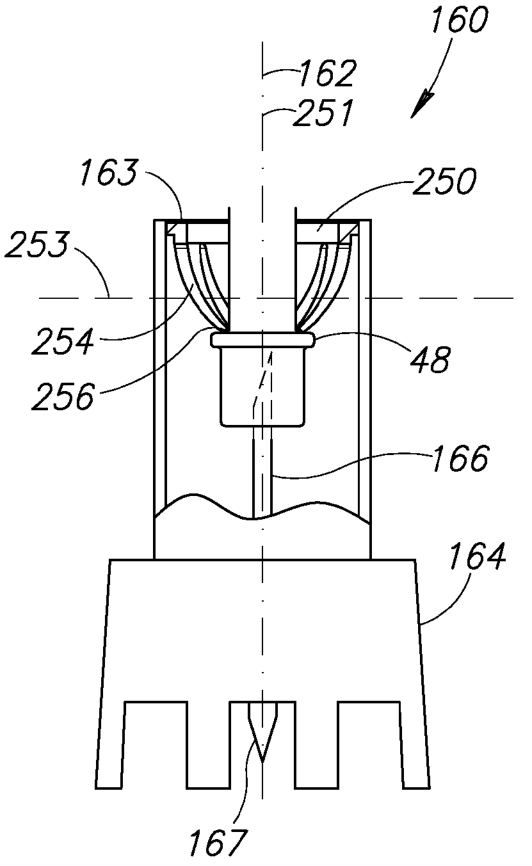
FIG. 40 is a longitudinal cross section of FIG. 34's liquid drug transfer device with FIG. 37's universal injection port connector mounted on FIG. 39's small injection port.

FIG. 40 shows the liquid drug transfer device 160 with the universal injection port connector 250 attached on the small injection port 41A.

Figure 41:
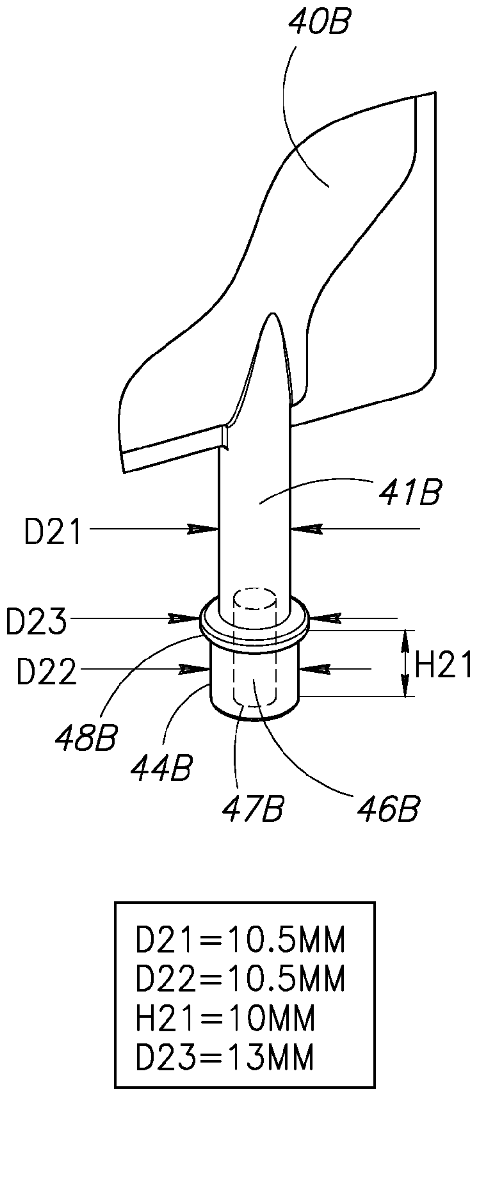
FIG. 41 is a front perspective view of an infusion bag with a so-called large injection port tip.

FIG. 41 shows an infusion bag 40B having a so-called large injection port 41B with the same construction as the small injection port 41A but with larger dimensions as follows: The injection port 41B has an external diameter D21. The injection port tip 44B has an external tip diameter D22 and a tip height H21. The trailing injection port tip rim 48B has an external diameter D23. D21 is 10.5 mm, D22 is 10.5 mm, H21 is 10 mm and D23 is 13 mm.

Figure 42:
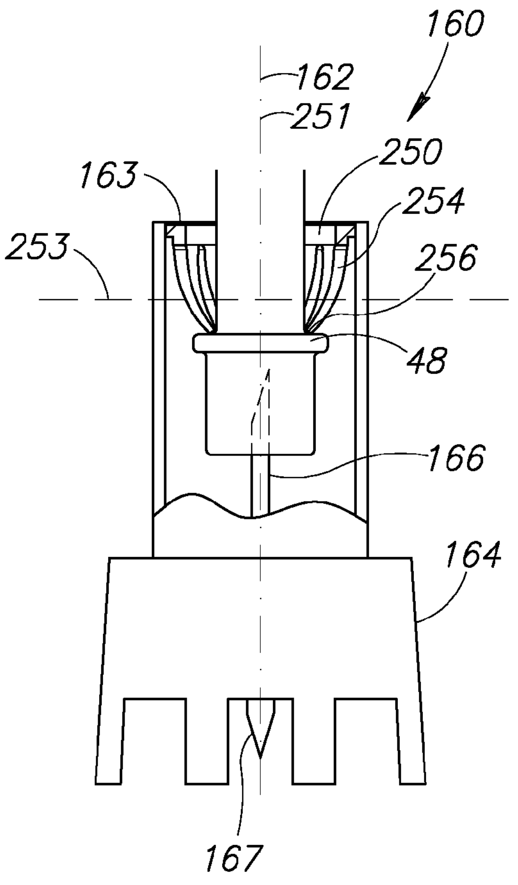
FIG. 42 is a longitudinal cross section of FIG. 34's liquid drug transfer device with FIG. 37's universal injection port connector mounted on FIG. 41's large injection port.

FIG. 42 shows the liquid drug transfer device 160 with the universal injection port connector 250 attached on the large injection port 41B. The connector members 254 are more steeply inclined when attaching the liquid drug transfer device 160 on the injection port 41B than the injection port 41A since the former 41B has a wider injection port diameter D21 than the latter 41A's injection port diameter D11.

While the invention has been described with respect to a limited number of embodiments, it will be appreciated that many variations, modifications, and other applications of the invention can be made within the scope of the appended claims.

The invention claimed is:

1. A liquid drug transfer device for use with a drug vial of a small drug vial and a large drug vial, the drug vial including a drug vial bottle, a drug vial interior, a drug vial stopper, an uppermost drug vial surface, and a drug vial closure, the small drug vial having a drug vial closure with an external diameter D1 and the large drug vial having a drug vial closure with an external diameter D2 where D2>D1 and the difference D2−D1 is in the range of between 4 mm and 7 mm, the liquid drug transfer device comprising an universal drug vial adapter having a longitudinal drug vial adapter axis and a skirt for telescopically clamping on the drug vial closure, said skirt including a top wall transverse to said longitudinal drug vial adapter axis, a first pair of axial directed, spaced apart flex member supports and a second pair of axial directed, spaced apart flex member supports opposite said first pair of axial directed flex member supports for defining a drug vial cavity for snugly telescopically receiving at least a top part of a large drug vial therein, each flex member support having a proximate end adjacent said top wall and a distal end remote from said top wall, said first pair of flex member supports including a first crosspiece extending between their corresponding distal ends, said first crosspiece integrally formed with an axial directed first flex member resiliently flexibly mounted thereon with respect to said longitudinal drug vial adapter axis, said first flex member having a first flex member free end remote from said first crosspiece and being axially directed and extending generally parallel to said longitudinal drug vial adapter axis from said first crosspiece to said first flex member free end, said first flex member further having an inward radial directed first drug vial grip, said second pair of flex member supports including a second crosspiece extending between their corresponding distal ends, said second crosspiece integrally formed with an axial directed second flex member resiliently flexibly mounted thereon with respect to said longitudinal drug vial adapter axis, said second flex member having a second flex member free end remote from said crosspiece and being axially directed and extending generally parallel to said longitudinal drug vial adapter axis from said second crosspiece to said second flex member free end, said second flex member further having an inward radial directed second drug vial grip, said first flex member and said second flex member being opposite such that said first drug vial grip and said second drug vial grip define a separation S therebetween where S<D1 whereupon said first drug vial grip and said second drug vial grip underlie a drug vial closure on telescopically clamping said universal drug vial adapter on the drug vial, said first flex member and said second flex member being outwardly resiliently flexed correspondingly at said first crosspiece and said second crosspiece with respect to said longitudinal drug vial adapter axis to a greater extent on telescopically clamping said universal drug vial adapter on the large drug vial compared to telescopically clamping said universal drug vial adapter on the small drug vial.

2. The device according to claim 1, wherein said skirt includes a single continuous annular support including said first crosspiece, said second crosspiece, a third crosspiece extending between said first crosspiece and said second crosspiece, and a fourth crosspiece extending between said first crosspiece and said second crosspiece and opposite said third crosspiece, said third crosspiece integrally formed with a third flex member resiliently flexibly mounted thereon with respect to said longitudinal drug vial adapter axis, said third flex member having a third flex member free end remote from said third crosspiece and being axially directed and extending generally parallel to said longitudinal drug vial adapter axis between said third crosspiece and said third flex member free end, said third flex member further having an inward radial directed third drug vial grip, and said fourth crosspiece integrally formed with a fourth flex member resiliently flexibly mounted thereon with respect to said longitudinal drug vial adapter axis, said fourth flex member having a fourth flex member free end remote from said fourth crosspiece and being axially directed and extending generally parallel to said longitudinal drug vial adapter axis between said fourth crosspiece and said fourth flex member free end, said fourth flex member further having an inward radial directed fourth drug vial grip, said third flex member and said fourth flex member being opposite such that said third drug vial grip and said fourth drug vial grip define said separation S therebetween whereupon said third drug vial grip and said fourth drug vial grip underlie the drug vial closure on telescopically clamping said universal drug vial adapter on the drug vial.

3. The device according to claim 1, wherein said top wall is constituted by an annular centerpiece and a radial strut from said annular centerpiece to each said flex member support.

4. The device according to claim 1, wherein said flex members are arranged to be generally parallel to said longitudinal drug vial adapter axis prior to telescopically clamping said universal drug vial adapter on a drug vial such that said first flex member and said second flex member are generally parallel to said longitudinal drug vial adapter axis on telescopically clamping said universal drug vial adapter on a small drug vial and are outwardly flexed with respect to said longitudinal drug vial adapter axis on telescopically mounting said universal drug vial adapter on a large drug vial.

5. The device according to claim 1, wherein said top wall includes an integral access port and an integral puncturing member in flow communication with said integral access port for puncturing a drug vial stopper on telescopic clamping said universal drug vial adapter on the drug vial for enabling flow communication with the drug vial interior.

6. The device according to claim 1, wherein said universal drug vial adapter is capable of being telescopically clamped on a pre-attached initially intact drug vial, said top wall including an axial directed tubular stem overlying the uppermost drug vial surface of the pre-attached initially intact drug vial, the liquid drug transfer device further comprising a discrete liquid transfer member with a puncturing tip disposed in said stem for puncturing the drug vial stopper on downward urging said liquid transfer member towards the drug vial for enabling flow communication with the drug vial interior.

7. The device according to claim 6, wherein said pre-attached intact drug vial is removable intact from said universal drug vial adapter on employing a drug vial release tool for outwardly flexing said flex members relative to said longitudinal drug vial adapter axis.

8. The device according to claim 1, wherein D1 is between 13 mm and 14 mm and D2 is between 20 mm and 21 mm.

9. A liquid drug transfer device for use with a drug vial of a small drug vial and a large drug vial, the drug vial including a drug vial bottle, a drug vial interior, a drug vial stopper, an uppermost drug vial surface, and a drug vial closure, the small drug vial having a drug vial closure with an external diameter D1 and the large drug vial having a drug vial closure with an external diameter D2 where D2>D1, the liquid drug transfer device comprising an universal drug vial adapter having a longitudinal drug vial adapter axis and a skirt for telescopically clamping on the drug vial closure, said skirt including a top wall transverse to said longitudinal drug vial adapter axis, a first pair of axial directed, spaced apart flex member supports and a second pair of axial directed, spaced apart flex member supports opposite said first pair of axial directed flex member supports for defining a drug vial cavity for snugly telescopically receiving at least a top part of a large drug vial therein, each flex member support having a proximate end adjacent said top wall and a distal end remote from said top wall, said first pair of flex member supports including a first crosspiece extending between their corresponding distal ends, said first crosspiece integrally formed with an axial directed first flex member resiliently flexibly mounted thereon with respect to said longitudinal drug vial adapter axis, said first flex member having a first flex member free end remote from said first crosspiece and being axially directed and extending generally parallel to said longitudinal drug vial adapter axis from said first crosspiece to said first flex member free end, said first flex member further having an inward radial directed first drug vial grip, said second pair of flex member supports including a second crosspiece extending between their corresponding distal ends, said second crosspiece integrally formed with an axial directed second flex member resiliently flexibly mounted thereon with respect to said longitudinal drug vial adapter axis, said second flex member having a second flex member free end remote from said crosspiece and being axially directed and extending generally parallel to said longitudinal drug vial adapter axis from said second crosspiece to said second flex member free end, said second flex member further having an inward radial directed second drug vial grip, said first flex member and said second flex member being opposite such that said first drug vial grip and said second drug vial grip define a separation S therebetween where S<D1 whereupon said first drug vial grip and said second drug vial grip underlie a drug vial closure on telescopically clamping said universal drug vial adapter on the drug vial, said first flex member and said second flex member being outwardly resiliently flexed correspondingly at said first crosspiece and said second crosspiece with respect to said longitudinal drug vial adapter axis to a greater extent on telescopically clamping said universal drug vial adapter on the large drug vial compared to telescopically clamping said universal drug vial adapter on the small drug vial.

10. The device according to claim 9, wherein said skirt includes a single continuous annular support including said first crosspiece, said second crosspiece, a third crosspiece extending between said first crosspiece and said second crosspiece, and a fourth crosspiece extending between said first crosspiece and said second crosspiece and opposite said third crosspiece, said third crosspiece integrally formed with a third flex member resiliently flexibly mounted thereon with respect to said longitudinal drug vial adapter axis, said third flex member having a third flex member free end remote from said third crosspiece and being axially directed and extending generally parallel to said longitudinal drug vial adapter axis between said third crosspiece and said third flex member free end, said third flex member further having an inward radial directed third drug vial grip, and said fourth crosspiece integrally formed with a fourth flex member resiliently flexibly mounted thereon with respect to said longitudinal drug vial adapter axis, said fourth flex member having a fourth flex member free end remote from said fourth crosspiece and being axially directed and extending generally parallel to said longitudinal drug vial adapter axis between said fourth crosspiece and said fourth flex member free end, said fourth flex member further having an inward radial directed fourth drug vial grip, said third flex member and said fourth flex member being opposite such that said third drug vial grip and said fourth drug vial grip define said separation S therebetween whereupon said third drug vial grip and said fourth drug vial grip underlie the drug vial closure on telescopically clamping said universal drug vial adapter on the drug vial.

11. The device according to claim 9, wherein said top wall is constituted by an annular centerpiece and a radial strut from said annular centerpiece to each said flex member support.

12. The device according to claim 9, wherein said flex members are arranged to be generally parallel to said longitudinal drug vial adapter axis prior to telescopically clamping said universal drug vial adapter on a drug vial such that said first flex member and said second flex member are generally parallel to said longitudinal drug vial adapter axis on telescopically clamping said universal drug vial adapter on a small drug vial and are outwardly flexed with respect to said longitudinal drug vial adapter axis on telescopically mounting said universal drug vial adapter on a large drug vial.

13. The device according to claim 9, wherein said top wall includes an integral access port and an integral puncturing member in flow communication with said integral access port for puncturing a drug vial stopper on telescopic clamping said universal drug vial adapter on the drug vial for enabling flow communication with the drug vial interior.

14. The device according to claim 9, wherein said universal drug vial adapter is capable of being telescopically clamped on a pre-attached initially intact drug vial, said top wall including an axial directed tubular stem overlying the uppermost drug vial surface of the pre-attached initially intact drug vial, the liquid drug transfer device further comprising a discrete liquid transfer member with a puncturing tip disposed in said stem for puncturing the drug vial stopper on downward urging said liquid transfer member towards the drug vial for enabling flow communication with the drug vial interior.

15. The device according to claim 14, wherein said pre-attached intact drug vial is removable intact from said universal drug vial adapter on employing a drug vial release tool for outwardly flexing said flex members relative to said longitudinal drug vial adapter axis.

* * * * *